United States Patent
Stransky et al.

(10) Patent No.: US 10,875,930 B2
(45) Date of Patent: Dec. 29, 2020

(54) PIK3C2G FUSIONS

(71) Applicant: Blueprint Medicines Corporation, Cambridge, MA (US)

(72) Inventors: Nicolas Stransky, Charlestown, MA (US); Ethan G. Cerami, Winchester, MA (US); Joseph L. Kim, Wayland, MA (US); Christoph Lengauer, Cambridge, MA (US)

(73) Assignee: BLUEPRINT MEDICINES CORPORATION, Cambridge, MA (US)

(*) Notice: Subject to any disclaimer, the term of this patent is extended or adjusted under 35 U.S.C. 154(b) by 0 days.

(21) Appl. No.: 14/909,038

(22) PCT Filed: Jul. 30, 2014

(86) PCT No.: PCT/US2014/048869
§ 371 (c)(1),
(2) Date: Jan. 29, 2016

(87) PCT Pub. No.: WO2015/017528
PCT Pub. Date: Feb. 5, 2015

(65) Prior Publication Data
US 2016/0251446 A1    Sep. 1, 2016

Related U.S. Application Data

(60) Provisional application No. 61/860,148, filed on Jul. 30, 2013.

(51) Int. Cl.
| | | |
|---|---|---|
| *C07K 16/40* | (2006.01) | |
| *C12Q 1/6886* | (2018.01) | |
| *C12Q 1/48* | (2006.01) | |
| *A61K 31/517* | (2006.01) | |
| *C12N 15/113* | (2010.01) | |
| *G01N 33/574* | (2006.01) | |

(52) U.S. Cl.
CPC ............ *C07K 16/40* (2013.01); *A61K 31/517* (2013.01); *C12N 15/1137* (2013.01); *C12Q 1/485* (2013.01); *C12Q 1/6886* (2013.01); *G01N 33/57492* (2013.01); *C07K 2317/33* (2013.01); *C07K 2317/34* (2013.01); *C12N 2310/14* (2013.01); *C12Q 2600/156* (2013.01); *C12Q 2600/158* (2013.01); *G01N 2333/91215* (2013.01); *G01N 2800/7028* (2013.01)

(58) Field of Classification Search
None
See application file for complete search history.

(56) References Cited

U.S. PATENT DOCUMENTS

2011/0319477 A1* 12/2011 Samuels .............. C12Q 1/6886
514/44 A

FOREIGN PATENT DOCUMENTS

| WO | WO 2008/008310 A2 | 1/2008 |
|---|---|---|
| WO | WO 2008/026075 A2 | 3/2008 |
| WO | WO 2009/140128 A2 | 11/2009 |
| WO | WO 2010/081001 A2 | 7/2010 |
| WO | WO 2013/074518 A1 | 5/2013 |

OTHER PUBLICATIONS

Mariuzza (Annu. Rev. Biophys. Biophys. Chem., 16: 139-159, 1987).*
Banerji, Shanatu, et al., "Sequence Analysis of mutations and translocations across breast cancer subtypes," Nature, 486: 405-409 (2012).
Howe, Louise R., et al., "Targeting the HER/EGFR/ErbB Family to Prevent Breast Cancer", Cancer Prevention Research, 4:1149-1157 (2011).
International Search Report and Written Opinion of International Application No. PCT/US2014/048869, dated Dec. 19, 2014 (19 pages).
Pei, Yanxin, et al. "An Animal Model of MYC-Driven Medulloblastoma," Cancer Cell, 21: 155-167 (2012).
Rosenthal, Andrew S., et al. "Potent and selective small molecule inhibitors of specific isoforms of Cdc2-like kinases (Cik) and dual specificity tyrosine-phosphorylation-regulated kinases (Dyrk)," Bioorganic & Medicinal Chemistry Letters, 21:3152-3158 (2011).
Soda, Manabu, et al., "Identification of the transforming EML4-ALK fusion gene in non-small-cell lung cancer," Nature, 448:561-566 (2007).
Stransky, Nicolas et al., "The landscape of kinase fusions in cancer," Nature Communications, vol. 5, Article No. 4846, doi:10.1038/ncomms5846 (2014), and "Supplementary Data 2: List of all recurrent kinase fusions and sample ids" retrieved from URL: http://www.nature.com/incomms/2014/140910/ncomms5846/extref/ncomms5846-s3.xlsx.
Tweives, Chris, et al., "Erlotinib in combination with capecitabine and docetaxel in patients with metastatic breast cancer: A dose-escalation study," European Journal of Cancer, 44:419-426 (2008).
Rozycka, Magdalena, et al., "cDNA Cloning of a Third Human C2-Domain-Containing Class II Phosphoinositide 3-Kinase, PI3K-C2g, and Chromosomal Assignment of This Gene (PIK3C2G) to 12p12," Genomics, 54: 569-74 (1998).

* cited by examiner

Primary Examiner — Nelson B Moseley, II

(74) Attorney, Agent, or Firm — Finnegan, Henderson, Farabow, Garrett & Dunner, LLP

(57) ABSTRACT

The invention provides to PIK3C2G (phosphatidylinositol-4-phosphate 3-kinase, catalytic subunit type 2 gamma) gene fusions and PIK3C2G fusion proteins. The invention further provides methods of diagnosing and treating diseases or disorders associated with PK3C2G fusions, such as conditions mediated by aberrant PIK3C2G expression or activity, or conditions associated with overexpression of PIK.3C2G.

5 Claims, 5 Drawing Sheets
Specification includes a Sequence Listing.

FIGURE 1

```
ATGGCGGCGG CTCCGCTGCT GCTGCTGCTG CTGCTCGTGC CCGTGCCGCT GCTGCCGCTG   60
CTGGCCCAAG GGCCCGGAGG GGCGCTGGGA AACCGGCATG CGGTGTACTG GAACAGCTCC  120
AACCAGCACC TGCGGCGAGA GGGCTACACC GTGCAGGTGA ACGTGAACGA CTATCTGGAT  180
ATTTACTGCC CGCACTACAA CAGCTCGGGG GTGGGCCCCG GGGCGGGACC GGGGCCCGGA  240
GGCGGGGCAG AGCAGTACGT GCTGTACATG GTGAGCCGCA ACGGCTACCG CACCTGCAAC  300
GCCAGCCAGG GCTTCAAGCG CTGGGAGTGC AACCGGCCGC ACGCCCCGCA CAGCCCCATC  360
AAGTTCTCGG AGAAGTTCCA GCGCTACAGC GCCTTCTCTC TGGGCTACGA GTTCCACGCC  420
GGCCACGAGT ACTACTACAT CT/GCTTGATA GAGAAGGTAA CAACTGAACT ATCCACATCC  480
ATCTACCAGC TAATCAATGT CTACTGTAAC AGCTTTTATG CAGATTTTCA GCCTGTAAAT  540
GTACCTAGAT GCACTTCCTA TCTAAATCCC GGGCTTCCTT CCCACCTCAG CTTCACAGTG  600
TATGCAGCAC ACAACATTCC AGAAACCTGG GTGCACAGGA TCAATTTTCC CCTTGAAATA  720
AAGTCACTTC CAAGGGAATC CATGCTCACT GTAAAACTGT TTGGGATTGC CTGTGCAACC  780
AACAATGCAA ATTTACTGGC GTGGACTTGT CTTCCACTGT TTCCAAAAGA AAAATCCATT  840
CTCGGGTCTA TGCTGTTCAG CATGACATTA CAGAGTGAGC CTCCCGTAGA AATGATAACT  900
CCAGGAGTGT GGGATGTAAG TCAGCCATCC CCGGTGACCC TGCAGATTGA TTTTCCAGCT  960
ACTGGGTGGG AGTATATGAA ACCTGATTCT GAAGAGAATA GAAGTAATCT TGAAGAGCCA 1020
CTAAAGGAGT GTATAAAACA TATTGCCAGA CTTTCACAGA AACAGACTCC CCTACTACTC 1080
TCTGAAGAAA AGAAAAGATA TTTATGGTTT TATCGCTTCT ACTGCAATAA TGAAAACTGC 1140
TCCCTTCCTT TAGTCCTGGG TAGTGCCCCT GGATGGGATG AAAGGACTGT TTCAGAAATG 1200
CATACCATTT TGAGAAGATG GACATTTTCT CAACCTTTAG AGGCTCTTGG GCTTTTGACT 1260
TCCAGTTTTC CAGATCAAGA AATTCGTAAA GTGGCAGTTC AACAATTAGA CAACCTCTTG 1320
AATGATGAAC TACTGGAATA TCTCCCACAG CTAGTTCAGG CTGTCAAGTT TGAATGGAAC 1380
CTTGAGAGTC CTTTAGTGCA ACTTCTACTC CACCGCTCCT TGCAGAGCAT CCAGGTTGCC 1440
CATCGTCTTT ACTGGCTGCT AAAAAATGCA GAAAATGAAG CTTATTTTAA AAGCTGGTAT 1500
CAGAAGCTAC TAGCTGCTCT CCAATTCTGT GCAGGTAAAG CCTTGAATGA TGAGTTTTCC 1560
AAGGAGCAGA AACTTATCAA AATTCTGGGA GATATTGGGG AAAGAGTCAA GTCTGCCAGT 1620
GACCATCAAA GACAGGAGGT ACTGAAGAAA GAAATTGGCA GACTAGAAGA GTTCTTTCAA 1680
GATGTAAATA CTTGTCATCT TCCTCTGAAC CCTGCCCTAT GTATAAAAGG GATTGATCAC 1740
GATGCATGTT CATATTTTAC ATCTAATGCT TTGCCATTGA AGATTACTTT CATCAATGCT 1800
AATCCGATGG GCAAAAACAT CAGCATTATT TTTAAGGCTG GAGATGATCT TCGTCAGGAT 1860
ATGCTTGTTC TGCAGCTTAT TCAAGTGATG GACAATATTT GGCTGCAGGA AGGCTTGGAT 1920
ATGCAAATGA TCATTTATAG ATGTCTATCC ACAGGAAAAG ACCAAGGATT GGTGCAGATG 1980
GTACCTGATG CTGTGACCCT AGCAAAGATT CATCGCCATT CTGGACTGAT AGGACCATTG 2040
AAAGAAAATA CAATTAAAAA GTGGTTCAGT CAGCACAACC ACTTAAAGGC AGATTATGAA 2100
AAGGCCTTGA GGAACTTTTT CTACTCCTGT GCTGGCTGGT GTGTGGTAAC ATTCATCCTG 2160
GGAGTATGTG ACCGTCACAA TGATAATATC ATGCTGACAA AGTCGGGCCA CATGTTTCAT 2220
ATTGACTTTG GAAAATTCTT AGGTCATGCA CAAACATTTG GAGGGATAAA AAGGGACCGA 2280
GCTCCTTTCA TTTTTACTTC AGAGATGGAA TACTTTATTA CAGAGGGTGG GAAAAACCCA 2340
CAGCATTTTC AAGATTTTGT GGAACTTTGC TGTCGTGCTT ATAATATTAT CAGAAAGCAC 2400
AGCCAACTGC TCTTGAACCT GCTGGAAATG ATGCTGTATG CAGGACTGCC TGAGCTAAGT 2460
GGAATTCAAG ACCTGAAATA TGTGTATAAT AATCTTCGTC CACAAGACAC AGACCTGGAA 2520
GCAACAAGTC ATTTTACCAA GAAAATAAAG GAAAGTCTGG AGTGTTTCCC TGTTAAATTG 2580
AATAACTTGA TCCACACACT TGCACAAATG TCAGCCATAA GCCCTGCCAA ATCTACTTCA 2640
CAGACTTTTC CTCAGGAATC CTGTTTGCTG AGTACAACTA GGTCGATTGA AAGAGCAACA 2700
ATTTTAGGGT TCAGCAAGAA ATCCAGTAAT CTGTATCTGA TCCAGGTGAC ACACAGCAAC 2760
AACGAAACAA GCCTGACAGA AAAATCATTT GAGCAGTTTT CAAAACTTCA CAGCCAACTT 2820
CAGAAGCAGT TTGCATCACT GACTCTCCCA GAGTTTCCTC ATTGGTGGCA CCTACCTTTT 2880
ACAAATTCAG ATCACAGAAG ATTCAGAGAT CTAAATCATT ACATGGAACA GATATTAAAT 2940
GTATCACATG AAGTTACAAA CAGTGATTGT GTACTTAGCT TTTTCCTCTC TGAGGCTGTG 3000
CAACAAACAG TTGAAGAATC ATCACCTGTG TACCTAGGTG AGAAGTTTCC AGACAAGAAG 3060
CCTAAGGTGC AGTTAGTCAT ATCCTACGAG GATGTGAAGC TGACCATACT AGTGAAACAC 3120
ATGAAAAACA TTCATCTCCC AGATGGCTCT GCGCCCAGTG CACATGTTGA ATTTTATCTT 3180
TTACCATATC CCAGTGAAGT TCGTAGGAGG AAAACAAAAT CTGTTCCAAA ATGTACGGAC 3240
CCCACTTACA ATGAAATTGT AGTATATGAT GAAGTCACAG AGCTCCAAGG ACATGTCTTA 3300
ATGCTTATTG TGAAGAGTAA AACTGTATTT GTGGGAGCAA TTAACATCCG ACTCTGTAGT 3360
GTCCCACTCG ATAAAGAAAA ATGGTATCCA TTAGGAAACA GTATAATTTG A (SEQ ID NO:1)
```

FIGURE 2

```
MAAAPLLLLL LLVPVPLLPL LAQGPGGALG NRHAVYWNSS NQHLRREGYT VQVNVNDYLD   60
IYCPHYNSSG VGPGAGPGPG GGAEQYVLYM VSRNGYRTCN ASQGFKRWEC NRPHAPHSPI  120
KFSEKFQRYS AFSLGYEFHA GHEYYYICLI EKVTTELSTS IYQLINVYCN SFYADFQPVN  180
VPRCTSYLNP GLPSHLSFTV YAAHNIPETW VHRINFPLEI KSLPRESMLT VKLFGIACAT  240
NNANLLAWTC LPLFPKEKSI LGSMLFSMTL QSEPPVEMIT PGVWDVSQPS PVTLQIDFPA  300
TGWEYMKPDS EENRSNLEEP LKECIKHIAR LSQKQTPLLL SEEKKRYLWF YRFYCNNENC  360
SLPLVLGSAP GWDERTVSEM HTILRRWTFS QPLEALGLLT SSFPDQEIRK VAVQQLDNLL  420
NDELLEYLPQ LVQAVKFEWN LESPLVQLLL HRSLQSIQVA HRLYWLLKNA ENEAYFKSWY  480
QKLLAALQFC AGKALNDEFS KEQKLIKILG DIGERVKSAS DHQRQEVLKK EIGRLEEFFQ  540
DVNTCHLPLN PALCIKGIDH DACSYFTSNA LPLKITFINA NPMGKNISII FKAGDDLRQD  600
MLVLQLIQVM DNIWLQEGLD MQMIIYRCLS TGKDQGLVQM VPDAVTLAKI HRHSGLIGPL  660
KENTIKKWFS QHNHLKADYE KALRNFFYSC AGWCVVTFIL GVCDRHNDNI MLTKSGHMFH  720
IDFGKFLGHA QTFGGIKRDR APFIFTSEME YFITEGGKNP QHFQDFVELC CRAYNIIRKH  780
SQLLLNLLEM MLYAGLPELS GIQDLKYVYN NLRPQDTDLE ATSHFTKKIK ESLECFPVKL  840
NNLIHTLAQM SAISPAKSTS QTFPQESCLL STTRSIERAT ILGFSKKSSN LYLIQVTHSN  900
NETSLTEKSF EQFSKLHSQL QKQFASLTLP EFPHWWHLPF TNSDHRRFRD LNHYMEQILN  960
VSHEVTNSDC VLSFFLSEAV QQTVEESSPV YLGEKFPDKK PKVQLVISYE DVKLTILVKH 1020
MKNIHLPDGS APSAHVEFYL LPYPSEVRRR KTKSVPKCTD PTYNEIVVYD EVTELQGHVL 1080
MLIVKSKTVF VGAINIRLCS VPLDKEKWYP LGNSII (SEQ ID NO:2)
```

FIGURE 3A

```
ATGTATGGAA GTGCCCGCTC TGTTGGGAAG GTGGAGCCGA GCAGCCAGAG CCCTGGGCGT    60
TCACCCAGGC TTCCACGTTC CCCTCGCTTG GGTCACCGTC GAACCAACAG TACGGGAGGG   120
AGTTCGGGAA GCAGTGTTGG AGGTGGCAGT GGGAAAACCC TTTCAATGGA AAATATACAA   180
TCTTTAAATG CTGCCTATGC CACCTCTGGC CCTATGTATC TAAGTGACCA TGAAAATGTG   240
GGTTCAGAAA CACCTAAAAG CACCATGACA CTTGGCCGTT CTGGGGGACG TCTGCCTTAC   300
GGTGTTCGGA TGACTGCTAT GGGTAGTAGC CCCAATATAG CTAGCAGTGG GGTTGCTAGT   360
GACACCATAG CATTTGGAGA GCATCACCTC CCTCCTGTGA GTATGGCATC CACTGTACCT   420
CACTCCCTTC GTCAGGCGAG AGATAACACA ATCATGGATC TGCAGACACA GCTGAAGGAA   480
GTATTAAGAG AAAATGATCT CTTGCGGAAG GATGTGGAAG TAAAGGAGAG CAAATTGAGT   540
TCTTCAATGA ATAGCATCAA GACCTTCTGG AGCCCAGAGC TGAAGAAGGA ACGAGCCCTG   600
AGAAAAGATG AAGCTTCCAA AATCACCATT TGGAAGGAAC AGTACAGAGT TGTACAGGAG   660
GAAAACCAGC ACATGCAGAT GACAATCCAG GCTCTCCAGG ATGAATTGCG GATCCAGAGG   720
GACCTGAATC AGCTGTTTCA GCAGGATAGT AGCAGCAGGA CTGGCGAACC TTGTGTAGCA   780
GAGCTGACAG AGGAGAACTT TCAGAGGCTT CATGCTGAGC ATGAGCGGCA GGCCAAAGAG   840
CTGTTTCTTC TTCGAAAGAC ATTGGAGGAA ATGGAGCTGC GTATTGAGAC TCAAAAGCAG   900
ACCCTAAATG CTCGGGATGA ATCCATTAAG AAGCTTCTGG AAATGTTGCA GAGCAAAGGA   960
CTTTCTGCCA AGGCTACCGA GGAAGACCAT GAGAGAACAA GACGACTGGC AGAGGCAGAG  1020
ATGCACGTTC ATCACCTAGA AAGCCTTTTG GAGCAGAAGG AAAAAGAGAA CAGTATGTTG  1080
AGAGAGGAGA TGCATCGAAG GTTTGAGAAT GCTCCTGATT CTGCCAAAAC AAAAGCTCTG  1140
CAAACTGTTA TTGAGATGAA GGATTCAAAA ATTTCCTCTA TGGAGCGTGG GCTTCGAGAC  1200
CTGGAAGAGG AAATTCAGAT GCTGAAATCG AATGGTGCTT TGAGTACTGA GGAAAGGGAA  1260
GAAGAAATGA AGCAAATGGA AGTGTATCGG AGCCATTCTA AATTTATGAA AAATAAGGTA  1320
GAACAACTGA AGGAGGAACT AAGTTCGAAA GAGGCTCAAT GGGAGGAGCT GAAAAAGAAA  1380
GCGGCTGGTC TTCAGGCTGA GATTGGCCAG GTGAAACAGG AGCTGTCCAG AAAGGACACA  1440
GAACTACTCG CCCTGCAGAC AAAGCTAGAA ACACTCACAA ACCAGTTCTC AGATAGTAAA  1500
CAGCACATTG AAGTGTTGAA GGAGTCCTTG ACTGCTAAGG AGCAGAGGGC TGCCATCCTG  1560
CAGACTGAGG TGGATGCTCT CCGATTGCGT TTGGAAGAGA AGGAAACCAT GTTGAATAAA  1620
AAGACAAAAC AAATTCAGGA TATGGCTGAA GAGAAGGGGA CACAAGCTGG AGAGATACAT  1680
GACCTCAAGG ACATGTTGGA TGTGAAGGAG CGGAAGGTTA ATGTTCTTCA GAAGAAGATT  1740
GAAAATCTTC AAGAGCAGCT TAGAGACAAG GAAAAGCAGA TGAGCAGCTT GAAAGAACGG  1800
GTCAAATCCT TGCAGGCTGA CACCACCAAC ACTGACACTG CCTTGACAAC TTTGGAGGAG  1860
GCCCTTGCAG AGAAAGAGCG GACAATTGAA CGCTTAAAGG AGCAGAGGGA CAGAGATGAG  1920
CGAGAGAAGC AAGAGGAAAT TGATAACTAC AAAAAAGATC TTAAAGACTT GAAGGAAAAA  1980
GTCAGCCTGT TGCAAGGCGA CCTTTCAGAG AAAGAGGCTT CACTTTTGGA TCTGAAAGAG  2040
CATGCTTCTT CTCTGGCATC CTCAGGACTG AAAAAGGACT CACGGCTTAA GACACTAGAG  2100
ATTGCTTTGG AGCAGAAGAA GGAGGAGTGT CTGAAAATGG AATCACAATT GAAAAAGGCA  2160
CATGAGGCAG CATTGGAAGC CAGAGCCAGT CCAGAGATGA GTGACCGAAT ACAGCACTTG  2220
GAGAGAGAGA TCACCAGGTA CAAAGATGAA TCTAGCAAGG CCCAGGCAGA AGTTGATCGA  2280
CTCTTAGAAA TCTTGAAGGA GGTGGAAAAT GAGAAGAATG ACAAAGATAA GAAGATAGCT  2340
GAGTTGGAAA G/GCTGCTAAA AAATGCAGAA AATGAAGCTT ATTTTAAAAG CTGGTATCAG  2400
AAGCTACTAG CTGCTCTCCA ATTCTGTGCA GGTAAAGCCT TGAATGATGA GTTTTCCAAG  2460
GAGCAGAAAC TTATCAAAAT TCTGGGAGAT ATTGGGGAAA GAGTCAAGTC TGCCAGTGAC  2520
CATCAAAGAC AGGAGGTACT GAAGAAAGAA ATTGGCAGAC TAGAAGAGTT CTTTCAAGAT  2580
GTAAATACTT GTCATCTTCC TCTGAACCCT GCCCTATGTA AAAAGGGAT TGATCACGAT  2640
GCATGTTCAT ATTTTACATC TAATGCTTTG CCATTGAAGA TTACTTTCAT CAATGCTAAT  2700
CCGATGGGCA AAAACATCAG CATTATTTTT AAGGCTGGAG ATGATCTTCG TCAGGATATG  2760
CTTGTTCTGC AGCTTATTCA AGTGATGGAC AATATTTGGC TGCAGGAAGG CTTGGATATG  2820
CAAATGATCA TTTATAGATG TCTATCCACA GGAAAAGACC AAGGATTGGT GCAGATGGTA  2880
CCTGATGCTG TGACCCTAGC AAAGATTCAT CGCCATTCTG GACTGATAGG ACCATTGAAA  2940
```

FIGURE 3B

```
GAAAATACAA TTAAAAAGTG GTTCAGTCAG CACAACCACT TAAAGGCAGA TTATGAAAAG  3000
GCCTTGAGGA ACTTTTTCTA CTCCTGTGCT GGCTGGTGTG TGGTAACATT CATCCTGGGA  3060
GTATGTGACC GTCACAATGA TAATATCATG CTGACAAAGT CGGGCCACAT GTTTCATATT  3120
GACTTTGGAA AATTCTTAGG TCATGCACAA ACATTTGGAG GGATAAAAAG GGACCGAGCT  3180
CCTTTCATTT TTACTTCAGA GATGGAATAC TTTATTACAG AGGGTGGGAA AAACCCACAG  3240
CATTTTCAAG ATTTTGTGGA ACTTTGCTGT CGTGCTTATA ATATTATCAG AAAGCACAGC  3300
CAACTGCTCT TGAACCTGCT GGAAATGATG CTGTATGCAG GACTGCCTGA GCTAAGTGGA  3360
ATTCAAGACC TGAAATATGT GTATAATAAT CTTCGTCCAC AAGACACAGA CCTGGAAGCA  3420
ACAAGTCATT TTACCAAGAA AATAAAGGAA AGTCTGGAGT GTTTCCCTGT TAAATTGAAT  3480
AACTTGATCC ACACACTTGC ACAAATGTCA GCCATAAGCC CTGCCAAATC TACTTCACAG  3540
ACTTTTCCTC AGGAATCCTG TTTGCTGAGT ACAACTAGGT CGATTGAAAG AGCAACAATT  3600
TTAGGGTTCA GCAAGAAATC CAGTAATCTG TATCTGATCC AGGTGACACA CAGCAACAAC  3660
GAAACAAGCC TGACAGAAAA ATCATTTGAG CAGTTTTCAA AACTTCACAG CCAACTTCAG  3720
AAGCAGTTTG CATCACTGAC TCTCCCAGAG TTTCCTCATT GGTGGCACCT ACCTTTTACA  3780
AATTCAGATC ACAGAAGATT CAGAGATCTA AATCATTACA TGGAACAGAT ATTAAATGTA  3840
TCACATGAAG TTACAAACAG TGATTGTGTA CTTAGCTTTT TCCTCTCTGA GGCTGTGCAA  3900
CAAACAGTTG AAGAATCATC ACCTGTGTAC CTAGGTGAGA AGTTTCCAGA CAAGAAGCCT  3960
AAGGTGCAGT TAGTCATATC CTACGAGGAT GTGAAGCTGA CCATACTAGT GAAACACATG  4020
AAAAACATTC ATCTCCCAGA TGGCTCTGCG CCCAGTGCAC ATGTTGAATT TTATCTTTTA  4080
CCATATCCCA GTGAAGTTCG TAGGAGGAAA ACAAAATCTG TTCCAAAATG TACGGACCCC  4140
ACTTACAATG AAATTGTAGT ATATGATGAA GTCACAGAGC TCCAAGGACA TGTCTTAATG  4200
CTTATTGTGA AGAGTAAAAC TGTATTTGTG GGAGCAATTA ACATCCGACT CTGTAGTGTC  4260
CCACTCGATA AAGAAAAATG GTATCCATTA GGAAACAGTA TAATTTGA   (SEQ ID NO:3)
```

FIGURE 4

```
MYGSARSVGK VEPSSQSPGR SPRLPRSPRL GHRRTNSTGG SSGSSVGGGS GKTLSMENIQ   60
SLNAAYATSG PMYLSDHENV GSETPKSTMT LGRSGGRLPY GVRMTAMGSS PNIASSGVAS  120
DTIAFGEHHL PPVSMASTVP HSLRQARDNT IMDLQTQLKE VLRENDLLRK DVEVKESKLS  180
SSMNSIKTFW SPELKKERAL RKDEASKITI WKEQYRVVQE ENQHMQMTIQ ALQDELRIQR  240
DLNQLFQQDS SSRTGEPCVA ELTEENFQRL HAEHERQAKE LFLLRKTLEE MELRIETQKQ  300
TLNARDESIK KLLEMLQSKG LSAKATEEDH ERTRRLAEAE MHVHHLESLL EQKEKENSML  360
REEMHRRFEN APDSAKTKAL QTVIEMKDSK ISSMERGLRD LEEEIQMLKS NGALSTEERE  420
EEMKQMEVYR SHSKFMKNKV EQLKEELSSK EAQWEELKKK AAGLQAEIGQ VKQELSRKDT  480
ELLALQTKLE TLTNQFSDSK QHIEVLKESL TAKEQRAAIL QTEVDALRLR LEEKETMLNK  540
KTKQIQDMAE EKGTQAGEIH DLKDMLDVKE RKVNVLQKKI ENLQEQLRDK EKQMSSLKER  600
VKSLQADTTN TDTALTTLEE ALAEKERTIE RLKEQRDRDE REKQEEIDNY KKDLKDLKEK  660
VSLLQGDLSE KEASLLDLKE HASSLASSGL KKDSRLKTLE IALEQKKEEC LKMESQLKKA  720
HEAALEARAS PEMSDRIQHL EREITRYKDE SSKAQAEVDR LLEILKEVEN EKNDKDKKIA  780
ELERLLKNAE NEAYFKSWYQ KLLAALQFCA GKALNDEFSK EQKLIKILGD IGERVKSASD  840
HQRQEVLKKE IGRLEEFFQD VNTCHLPLNP ALCIKGIDHD ACSYFTSNAL PLKITFINAN  900
PMGKNISIIF KAGDDLRQDM LVLQLIQVMD NIWLQEGLDM QMIIYRCLST GKDQGLVQMV  960
PDAVTLAKIH RHSGLIGPLK ENTIKKWFSQ HNHLKADYEK ALRNFFYSCA GWCVVTFILG 1020
VCDRHNDNIM LTKSGHMFHI DFGKFLGHAQ TFGGIKRDRA PFIFTSEMEY FITEGGKNPQ 1080
HFQDFVELCC RAYNIIRKHS QLLLNLLEMM LYAGLPELSG IQDLKYVYNN LRPQDTDLEA 1140
TSHFTKKIKE SLECFPVKLN NLIHTLAQMS AISPAKSTSQ TFPQESCLLS TTRSIERATI 1200
LGFSKKSSNL YLIQVTHSNN ETSLTEKSFE QFSKLHSQLQ KQFASLTLPE FPHWWHLPFT 1260
NSDHRRFRDL NHYMEQILNV SHEVTNSDCV LSFFLSEAVQ QTVEESSPVY LGEKFPDKKP 1320
KVQLVISYED VKLTILVKHM KNIHLPDGSA PSAHVEFYLL PYPSEVRRRK TKSVPKCTDP 1380
TYNEIVVYDE VTELQGHVLM LIVKSKTVFV GAINIRLCSV PLDKEKWYPL GNSII
(SEQ ID NO:4)
```

PIK3C2G FUSIONS

This application is a U.S. national stage of International Patent Application No. PCT/US2014/048869, filed Jul. 30, 2014, which claims priority to U.S. Provisional application Ser. No. 61/860,148, filed Jul. 30, 2013, the contents of both of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 13, 2014, is named 12386.0002-00304_SL.txt and is 32,895 bytes in size.

FIELD OF THE INVENTION

This invention relates to PIK3C2G (phosphatidylinositol-4-phosphate 3-kinase, catalytic subunit type 2 gamma) gene fusions and PIK3C2G fusion proteins. The invention further relates to methods of diagnosing and treating diseases or disorders associated with PIK3C2G fusions, such as conditions mediated by PIK3C2G activity, or conditions associated with aberrant expression or overexpression of PIK3C2G.

BACKGROUND

Many forms of cancer are caused by genetic lesions that give rise to tumor initiation and growth. Genetic lesions may include chromosomal aberrations, such as translocations, inversions, deletions, copy number changes, gene expression level changes, and somatic and germline mutations. Indeed, the presence of such genomic aberrations is a hallmark feature of many cancers, including, for example, B cell cancer, lung cancer, breast cancer, ovarian cancer, pancreatic cancer, and colon cancer. In some models, cancer represents the phenotypic end-point of multiple genetic lesions that endow cells with a full range of biological properties required for tumorigenesis.

Recent efforts by The Cancer Genome Atlas (TCGA), the International Cancer Genome Consortium (ICGC), and dozens of other large-scale profiling efforts have generated an enormous amount of new sequencing data for dozens of cancer types—this includes whole-genome DNA, whole-exome DNA, and full-transcriptome RNA sequencing. These efforts have led to the identification of new driver genes and fusion genes within multiple cancer types. Fusions, particularly fusions involving kinases, are of particular interest, as such fusions have been shown to be oncogenic, and have been successfully targeted by new therapeutics. For example, anaplastic lymphoma kinase (ALK), one of the receptor tyrosine kinases, is known to become oncogenic when fused with various genes. See, e.g., M. Soda et al, "Identification of the transforming EML4-ALK fusion gene in non-small-cell lung cancer," *Nature* 444:561-566 (2007).

A need exists for identifying novel genetic lesions associated with cancer. For example, the presence of fusions involving a kinase in samples collected from more than one source can indicate that the kinase is an oncogenic driver. The identification of such fusions can be an effective approach to diagnosis of cancers and development of compounds, compositions, methods, and assays for evaluating and treating cancer patients,

SUMMARY

In one aspect, the invention provides methods for detecting the presence of a PIK3C2G fusion in a biological sample. The methods include the steps of: (a) obtaining a biological sample from a mammal; and (b) contacting the sample with a reagent that detects a PIK3C2G fusion, to determine whether a PIK3C2G fusion is present in the biological sample. In some embodiments, the sample can be from, e.g., a cancer patient, such as, e.g., a breast cancer patient. In some embodiments, the fusion can be, e.g., an EFNA3:PIK3C2G fusion or an ERC1:PIK3C2G fusion. In some embodiments, the EFNA3:PIK3C2G fusion has all or a part of the nucleotide and/or amino acid sequence (such as, e.g., the fusion junction) set forth in SEQ ID NO:1 and SEQ ID NO:2, respectively. In some embodiments, the ERC1:PIK3C2G fusion has all or part of the nucleotide and/or amino acid sequence (such as, e.g., the fusion junction) set forth in SEQ ID NO:3 and SEQ ID NO:4, respectively.

In another aspect, the invention provides methods of diagnosing a patient of having a disease or disorder associated with aberrant PIK3C2G activity or expression, or overexpression of PIK3C2G; the methods include: (a) obtaining a biological sample from the patient; and (b) contacting the sample with a reagent that detects a PIK3C2G fusion to determine whether a PIK3C2G fusion is present in the biological sample, whereby the detection of the PIK3C2G fusion indicates the presence of a disorder associated with aberrant PIK3C2G expression or activity or overexpression of PIK3C2G.

The invention also includes methods of determining a therapeutic regimen for treating a cancer in a human subject; methods of identifying a patient likely to respond to treatment with a PIK3C2G inhibitor or a PIK3C2G fusion inhibitor; methods of stratifying a patient population by detecting a PIK3C2G fusion; methods of treating a patient; a method of inhibiting the proliferation of cells containing a PIK3C2G fusion; methods of reducing an activity of a PIK3C2G fusion; methods of treating a condition mediated by aberrant PIK3C2G expression or activity; methods of treating a condition characterized by overexpression of PIK3C2G; methods of identifying an agent that modulates the activity of a PIK3C2G fusion; and methods of monitoring disease burden in a patient having a condition mediated by PIK3C2G.

BRIEF DESCRIPTION OF THE FIGURES

FIG. 1 depicts the nucleotide sequence of an EFNA3:PIK3C2G gene fusion (SEQ ID NO:1) comprising a portion of the EFNA3 gene (NM_004952) up to and including exon 2 (amino acid number 147) and a portion of the PIK3C2G gene (NM_004570) starting at exon 21 (amino acid number 478). The underlined codons at nucleotides 439-441 and 445-448 encode the last amino acid of EFNA3 and the first amino acid of PIK3C2G, respectively. The slash after nucleotide 442 indicates the breakpoint (fusion junction) where translocation and in-frame fusion has occurred. The shading at nucleotides 442-444 indicates that nucleotides from both EFNA3 and PIK3C2G are fused in frame to form a codon and encode an amino acid.

FIG. 2 depicts the amino acid sequence of an EFNA3:PIK3C2G fusion protein (SEQ ID NO:2). The shaded amino acid at position 148 corresponds to nucleotides 442-444 in SEQ ID NO:1. This amino acid is encoded by nucleotides from both EFNA3 and PIK3C2G.

FIG. 3A-3B depicts the nucleotide sequence of an ERC1:PIK3C2G gene fusion (SEQ ID NO:3) comprising a portion of the ERC1 gene (NM_178040) up to and including exon 12 (amino acid number 783) and a portion of the PIK3C2G gene (NM_004570) starting at exon 18 (amino acid number 795). The underlined codons at nucleotides 2347-2349 and 2353-2355 encode the last amino acid of ERC1 and the first amino acid of PIK3C2G, respectively. The slash after nucleotide 2351 indicates the breakpoint (fusion junction) where translocation and in-frame fusion has occurred. The shading at nucleotides 2350-2352 indicates that nucleotides from both ERC1 and PIK3C2G are fused in frame to form a codon and encode an amino acid.

FIG. 4 depicts the amino acid sequence of an ERC1:PIK3C2G fusion protein (SEQ ID NO:4). The shaded amino acid at position 784 corresponds to nucleotides 2350-2352 in SEQ ID NO:3. This amino acid is encoded by nucleotides from both ERC1 and PIK3C2G.

EXEMPLARY EMBODIMENTS OF THE INVENTION

The invention is based, at least in part, on the discovery of novel recombination or translocation events in cancer patients that result in at least a fragment of a PIK3C2G gene linked to a non-homologous promoter via a recombination or translocation event that may result in overexpression of the kinase domain of the PIK3C2G gene and thus, an increase in kinase activity, or aberrant expression due to the kinase being expressed in a location where it is not typically expressed. Thus, a new patient population is identified, which is characterized by the presence of a PIK3C2G fusion, e.g., a PIK3C2G gene fusion or fusion protein. This new patient population suffers from or is susceptible to disorders mediated by aberrant PIK3C2G expression or activity, or overexpression of PIK3C2G, such as, e.g., a cancer. In another aspect of the invention, a new subtype of cancer is identified, which is characterized by the presence of the PIK3C2G fusions described herein. In some embodiments, the new patient population suffers from or is susceptible to a breast cancer characterized by the presence of a PIK3C2G fusion. New methods of diagnosing and treating the patient population and the PIK3C2G fusion cancer subtype are also provided.

The term "PIK3C2G fusion" is used generically herein, and includes any fusion molecule (e.g., gene, gene product (e.g., cDNA, mRNA, or polypeptide), and variants thereof) that includes a fragment of PIK3C2G (in the case of a nucleotide sequence, the coding region for the kinase domain of PIK3C2G), and a non-homologous fragment (in the case of a nucleotide sequence, the promoter and/or the coding region of a non-homologous gene, such that the coding sequence for the kinase domain of PIK3C2G is under control of the promoter). A PIK3C2G fusion protein generally includes the kinase domain of PIK3C2G. In some embodiments, a PIK3C2G fusion is an EFNA3:PIK3C2G fusion. In some embodiments, a PIK3C2G fusion is an ERC1:PIK3C2G fusion.

PIK3C2G Gene Fusions and Fusion Proteins

PIK3C2G gene fusions are generated by a fusion between at least a part of the PIK3C2G gene and a part of another gene as a result of a translocation (including inversion) within a chromosome or between chromosomes. As a result of a translocation, the PIK3C2G gene may be placed under the transcriptional control of the partner gene promoter, resulting in aberrant PIK3C2G expression or activity, or overexpression of PIK3C2G. As used herein, the 5'-region is upstream of, and the 3'-region is downstream of, a fusion junction or breakpoint in one of the component genes. PIK3C2G and the gene or protein that it is fused to may be referred to as "fusion partners." Alternatively, they may be identified as a "PIK3C2G gene fusion" or a "PIK3C2G fusion protein," which are collectively termed "PIK3C2G fusions." The PIK3C2G fusions disclosed herein have a kinase activity. The phrase "having a kinase activity" as used in this application means having an activity as an enzyme phosphorylating a lipid, more specifically phosphatidylinositol, or as an enzyme phosphorylating the side chain of an amino acid, such as serine and/or threonine. In some embodiments, the PIK3C2G fusion may include an in-frame fusion of the coding sequences of PIK3C2G and the fusion partner that introduces amino acids into the fusion protein that are not part of PIK3C2G or the fusion partner.

Reference to "all or a portion" or "all or part" of a PIK3C2G gene fusion or SEQ ID NO:1 or SEQ ID NO:3, means that the nucleotide sequence comprises the entire PIK3C2G gene fusion nucleotide sequence or a fragment of that sequence that comprises the fusion junction breakpoint point between PIK3C2G and its fusion partner (such as, e.g., EFNA3 or ERC1). The fragment may comprise 7, 8, 9, 10, 12, 14, 16, 18, 20, 21, 22, 23, 24, 25, 26, 27, 28, 29, 30, 35, 40, 45, 50, 60, 70, 80, 90, 100, 120, 150, 175, 200, 250, 300, or more nucleotides spaning the fusion junction of the PIK3C2G gene fusion. Reference to "all or a portion" or "all or part" of a PIK3C2G fusion protein or SEQ ID NO:2 or SEQ ID NO:4, means an amino acid sequence that comprises the entire PIK3C2G fusion protein amino acid sequence or a fragment of that sequence that comprises the fusion junction breakpoint point between PIK3C2G and its fusion partner (such as, e.g., EFNA3 or ERC1). The fragment may comprise 8, 10, 12, 14, 15, 16, 18, 20, 21, 22, 23, 24, 25, 26, 27, 28, 29, 30, 35, 40, 45, 50, 75, or more amino acids spaning the fusion junction.

In some exemplary embodiments, the fusion partner is all or a portion of EFNA3 (Ephrin A3). In other exemplary embodiments, the fusion partner is all or a portion of ERC1 (ELKS/RAB6-Interacting/CAST Family Member 1).

In certain embodiments, a fusion includes an in-frame fusion of all or a portion of the EFNA3 gene (e.g., an EFNA3 promotor or a functional fragment thereof and one or more exons encoding EFNA3 or a fragment thereof) and an exon of the PIK3C2G gene (e.g., one or more exons encoding a PIK3C2G kinase domain or a functional fragment thereof). Such a fusion can be referred to as an EFNA3:PIK3C2G fusion. In one embodiment, the EFNA3:PIK3C2G fusion comprises sufficient EFNA3 and sufficient PIK3C2G sequences to drive expression of a fusion protein that has kinase activity. In some embodiments, the EFNA3:PIK3C2G fusion drives expression of a fusion protein that has elevated PIK3C2G activity as compared with wild type PIK3C2G in the same tissue or cell.

In a particular embodiment, the invention provides an EFNA3:PIK3C2G gene fusion comprising the nucleotide sequence depicted in FIG. 1 (SEQ ID NO:1), or a fragment thereof that includes the fusion junction. SEQ ID NO:1 comprises EFNA3 (NM_004952) through part of exon 2 (amino acid number 147) fused to PIK3C2G (NM_004570), from exon number 21 (amino acid number 478). In some embodiments the EFNA3:PIK3C2G gene fusion comprises a nucleotide sequence that is at least 85%, at least 90%, at least 95%, at least 97%, or at least 98% identical to all or part of SEQ ID NO: 1. In some embodiments, the EFNA3:PIK3C2G gene fusion encodes a protein having all or part of the sequence depicted in FIG. 2 (SEQ ID NO:2) or a sequence that is at least 85%, at least 90%, at least 95%, at least 97%, or at least 98% identical to all or part of SEQ ID NO:2.

In some embodiments, a fusion includes an in-frame fusion of all or a portion of the ERC1 gene (e.g., an ERC1 promotor or a functional fragment thereof and one or more exons encoding ERC1 or a fragment thereof) and an exon of the PIK3C2G gene (e.g., one or more exons encoding a PIK3C2G kinase domain or a functional fragment thereof). Such a fusion can be referred to as an ERC1:PIK3C2G fusion. In one embodiment, the ERC1:PIK3C2G fusion comprises sufficient ERC1 and sufficient PIK3C2G sequences to drive expression of a fusion protein that has a kinase activity. In some embodiments, the ERC1:PIK3C2G fusion drives expression of a fusion protein that has elevated PIK3C2G activity as compared with wild type PIK3C2G in the same tissue or cell.

In a particular embodiment, the ERC1:PIK3C2G fusion has the nucleotide sequence depicted in FIG. 3 (SEQ ID NO:3), or a fragment thereof that includes the fusion junction. SEQ ID NO:3 comprises ERC1 (NM_178040) up to exon 12 (amino acid number 783) fused to PIK3C2G (NM_004570), from exon 18 (amino acid number 795). In some embodiments the ERC1:PIK3C2G gene fusion comprises a nucleotide sequence that is at least 85%, at least 90%, at least 95%, at least 97%, or at least 98% identical to all or part of SEQ ID NO:3. In some embodiments, the ERC1:PIK3C2G fusion encodes a protein having all or part of the sequence depicted in FIG. 4 (SEQ ID NO:4) or a sequence that is at least 85%, at least 90%, at least 95%, at least 97%, or at least 98% identical to all or part of SEQ ID NO:4.

The nucleic acid sequences of PIK3C2G fusions may be used as probes, primers, or bait to identify nucleotides from a biological sample that include, flank, or hybridize to PIK3C2G fusions, such as EFNA3:PIK3C2G (SEQ ID NO: 1) or ERC1:PIK3C2G (SEQ ID NO:3), at, e.g., the fusion junctions. In certain embodiments, the probe, primer, or bait molecule is an oligonucleotide that allows capture, detection, or isolation of a PIK3C2G gene fusion in a biological sample. In certain embodiments, the probes or primers derived from the nucleic acid sequences of PIK3C2G gene fusions (e.g., from the fusion junctions) may be used, for example, for polymerase chain reaction (PCR) amplification. The oligonucleotide can comprise a nucleotide sequence substantially complementary to a fragment of the PIK3C2G gene fusion nucleic acid molecules described herein. The sequence identity between the nucleic acid fragment, e.g., the oligonucleotide and the target PIK3C2G gene fusion sequence, need not be exact, so long as the sequences are sufficiently complementary to allow the capture, detection, or isolation of the target sequence. In one embodiment, the nucleic acid fragment is a probe or primer that includes an oligonucleotide between about 5 and 25, e.g., between 10 and 20, or 10 and 15 nucleotides in length that includes the fusion junction of a PIK3C2G fusion, such as, e.g., EFNA3:PIK3C2G (SEQ ID NO: 1) or ERC1:PIK3C2G (SEQ ID NO:3). In other embodiments, the nucleic acid fragment is a bait that includes an oligonucleotide between about 100 to 300 nucleotides, 130 and 230 nucleotides, or 150 and 200 nucleotides in length that includes the fusion junction of a PIK3C2G fusion, such as, e.g., EFNA3:PIK3C2G (SEQ ID NO: 1) or ERC1:PIK3C2G (SEQ ID NO:3).

In certain embodiments, the nucleic acid fragments hybridize to a nucleotide sequence that includes a breakpoint or fusion junction, e.g., a breakpoint or fusion junction as identified by a slash ("/") in FIG. 1 or 3. For example, the nucleic acid fragment can hybridize to a nucleotide sequence that includes the fusion junction between the EFNA3 transcript and the PIK3C2G transcript (e.g, nucleotides 442-444 of SEQ ID NO: 1), or between the ERC1 transcript and the PIK3C2G transcript (e.g., nucleotides 2350-2352 of SEQ ID NO:3), i.e., a nucleotide sequence that includes a portion of SEQ ID NO: 1 or 3. Examples include a nucleotide sequence within exons 1-2 of an EFNA3 gene and exons 11-32 of a PIK3C2G gene (e.g., a portion of SEQ ID NO:1 comprising nucleotides 438-447, 433-452, 423-462, 393-492, 338-517, or 343-542); or a nucleotide sequence within exons 1-12 of an ERC1 gene and exons 18-32 of a PIK3C2G gene (e.g., a portion of SEQ ID NO:3 comprising nucleotides 2347-2356, 2342-2361, 2332-2371, 2302-2401, 2247-2426, or 2252-2451).

In other embodiments, the nucleic acid fragment includes a bait that comprises a nucleotide sequence that hybridizes to a PIK3C2G gene fusion nucleic acid molecule described herein, and thereby allows the detection, capture, and/or isolation of the nucleic acid molecule. In one embodiment, a bait is suitable for solution phase hybridization. In other embodiments, a bait includes a binding entity or detection entity, e.g., an affinity tag or fluorescent label, that allows detection, capture, and/or separation, e.g., by binding to a binding entity, of a hybrid formed by a bait and a nucleic acid hybridized to the bait.

In exemplary embodiments, the nucleic acid fragments used as bait comprise a nucleotide sequence that includes a fusion junction between the EFNA3 transcript and the PIK3C2G transcript, e.g, a nucleotide sequence within SEQ ID NO:1 comprising nucleotides 442-444 (such as, e.g., a sequence comprising nucleotides 438-447, 433-452, 423-462, 393-492, 338-517, or 343-542 of SEQ ID NO:1). In another exemplary embodiment, the nucleic acid sequences hybridize to a nucleotide sequence that include a fusion junction between the ERC1 transcript and the PIK3C2G transcript, e.g., a nucleotide sequence within SEQ ID NO:3 comprising nucleotides 2350-2352 (such as, e.g., a sequence comprising nucleotides 2347-2356, 2342-2361, 2332-2371, 2302-2401, 2247-2426, or 2252-2451 of SEQ ID NO:3).

Another aspect of the invention provides PIK3C2G fusion proteins (such as, e.g., a purified or isolated EFNA3: PIK3C2G fusion protein or ERC1:PIK3C2G fusion protein), biologically active or antigenic fragments thereof, and use of those polypeptides for detecting and/or modulating the biological activity (such as tumorigenic activity) of a PIK3C2G fusion protein. Exemplary embodiments of the PIK3C2G fusion proteins comprise the amino acid sequence set forth in SEQ ID NO:2 or SEQ ID NO:4, and fragments of those sequences.

In some embodiments, the PIK3C2G fusion protein of the invention includes a fragment of an EFNA3 protein or an ERC1 protein and a fragment of a PIK3C2G protein. In certain embodiments, the PIK3C2G fusion protein is EFNA3:PIK3C2G fusion protein having the amino acid sequence of SEQ ID NO:2 or a fragment thereof, such as, e.g., amino acids 146-150, 143-153, 138-157, or 128-167 of SEQ ID NO:2. In certain embodiments, the PIK3C2G fusion protein is an ERC1:PIK3C2G fusion protein having the amino acid sequence of SEQ ID NO:4 or a fragment thereof, such as, e.g., amino acids 782-786, 778-787, 774-793, or 764-803 of SEQ ID NO:4. In yet another embodiment, the PIK3C2G fusion protein is an EFNA3:PIK3C2G fusion protein comprising an amino acid sequence that is at least 85%, at least 90%, at least 95%, at least 97%, or at least 98% identical to SEQ ID NO:2 or a fragment thereof (e.g., amino acids 146-150, 143-153, 138-157, or 128-167 of SEQ ID NO:2). In another embodiment, the PIK3C2G fusion protein is an ERC1:PIK3C2G fusion protein comprising an amino acid sequence that is at least 85%, at least 90%, at least 95%, at least 97%, or at least 98% identical to SEQ ID NO:4 or a fragment thereof (e.g., amino acids 782-786, 778-787, 774-793, or 764-803 of SEQ ID NO:4).

In certain embodiments, the PIK3C2G fusion protein includes a functional kinase domain. In such embodiments, the PIK3C2G fusion protein possesses elevated activity, as compared with wild type PIK3C2G, for example, in a cancer cell, a non-cancer cell adjacent to the cancer cell, or a non-cancer cell from a control sample, such as a cancer free subject. In one exemplary embodiment, the PIK3C2G fusion protein is an EFNA3:PIK3C2G fusion and includes a PIK3C2G kinase domain or a functional fragment thereof. In another exemplary embodiment, the PIK3C2G fusion protein is an ERC1:PIK3C2G fusion and includes a PIK3C2G kinase domain or a functional fragment thereof.

In another embodiment, the PIK3C2G fusion protein or fragment is a peptide, e.g., an immunogenic peptide or protein, that contains a fusion junction with a heterologous protein as described herein. Such immunogenic peptides or proteins can be used for vaccine preparation for use in the treatment or prevention of cancers cause by or exacerbated by PIK3C2G gene fusions and PIK3C2G fusion proteins. In other embodiments, such immunogenic peptides or proteins can be used to raise antibodies specific to the fusion protein. In some embodiments, the PIK3C2G fusion protein is present in combination with or is further conjugated to one or more adjuvant(s) or immunogen(s), e.g., a protein capable of enhancing an immune response to the PIK3C2G fusion protein (e.g., a hapten, a toxoid, etc.). In some embodiments, the PIK3C2G fusion protein is an EFNA3:PIK3C2G or an ERC1:PIK3C2G fusion. In some embodiments, the PIK3C2G fusion protein comprises the fusion junction of SEQ ID NO:2 or SEQ ID NO:4.

Thus, another aspect of the invention provides an antibody that binds to a PIK3C2G fusion protein (such as, e.g., an EFNA3:PIK3C2G fusion protein or an ERC1:PIK3C2G fusion protein) or a fragment thereof. In certain embodiments, the antibody recognizes a PIK3C2G fusion protein but does not recognize wild type PIK3C2G or the wild type fusion partner (such as, e.g., EFNA3 or ERC1). In some embodiments, the antibody binds to an epitope comprising the fusion junction between PIK3C2G and the fusion partner (e.g., the fusion junction of EFNA3:PIK3C2G or ERC1: PIK3C2G). In one embodiment, the antibody binds to an EFNA3:PIK3C2G fusion protein having the amino acid sequence of SEQ ID NO:2 or a fragment thereof, such as, e.g., amino acids 146-150, 143-153, 138-157, or 128-167 of SEQ ID NO:2. In other embodiments, the antibody binds to an ERC1:PIK3C2G fusion protein having the amino acid sequence of SEQ ID NO:4 or a fragment thereof, such as, e.g., amino acids 782-786, 778-787, 774-793, or 764-803 of SEQ ID NO:4.

In certain embodiments, the antibodies of the invention inhibit and/or neutralize the biological activity of the PIK3C2G fusion protein, and more specifically, in some embodiments, the kinase activity of the PIK3C2G fusion protein. In other embodiments, the antibodies may be used to detect a PIK3C2G fusion protein or to diagnose a patient suffering from a disease or disorder associated with the expression of a PIK3C2G fusion protein.

Detection and Diagnostic Methods

In another aspect, the invention provides a method of determining the presence of a PIK3C2G gene fusion or fusion protein, such as, e.g., an EFNA3:PIK3C2G or an ERC1:PIK3C2G fusion as described herein. The presence of a PIK3C2G gene fusion can indicate that the mammal providing the biological sample suffers from or is at risk of developing a disorder mediated by aberrant PIK3C2G expression or activity, or overexpression of PIK3C2G, such as, e.g., a cancer. The presence of a PIK3C2G gene fusion may also indicate that the cancer is treatable with a PIK3C2G inhibitor (such as, e.g., an antibody specific to PIK3C2G) or a PIK3C2G fusion inhibitor.

In one embodiment, the PIK3C2G fusion detected is a nucleic acid molecule or a polypeptide. The method includes detecting whether a PIK3C2G fusion nucleic acid molecule or polypeptide is present in a cell (e.g., a circulating cell or a cancer cell), a tissue (e.g., a tumor), or a sample (e.g., a tumor sample), from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample. The sample can be chosen from one or more of sample types: such as, e.g., tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow.

In some embodiments, the PIK3C2G fusion (such as, e.g., EFNA3:PIK3C2G or ERC1:PIK3C2G, as disclosed herein) is detected in a nucleic acid molecule by one or more methods chosen from nucleic acid hybridization assays (e.g. in situ hybridization, comparative genomic hybridization, microarray, Southern blot, northern blot), amplification-based assays (e.g., PCR, PCR-RFLP assay, or real-time PCR), sequencing and genotyping (e.g. sequence-specific primers, high-performance liquid chromatography, or mass-spectrometric genotyping), and screening analysis (including metaphase cytogenetic analysis by karyotype methods).

Hybridization Methods

In some embodiments, the reagent hybridizes to a PIK3C2G gene fusion, such as, e.g., nucleotides 438-447, 433-452, 423-462, 393-492, 338-517, or 343-542 of SEQ ID NO:1. In alternate embodiments, the reagent detects the presence of nucleotides 2347-2356, 2342-2361, 2332-2371, 2302-2401, 2247-2426, or 2252-2451 of SEQ ID NO:3.

In another embodiment, the method of detecting the presence of a PIK3C2G gene fusion comprises the steps of obtaining a biological sample; exposing the sample to a nucleic acid probe which hybridizes to an mRNA or cDNA encoding a PIK3C2G fusion protein that comprises amino acids 146-150, 143-153, 138-157, or 128-167 of SEQ ID NO:2 or amino acids 782-786, 778-787, 774-793, or 764-803 of SEQ ID NO:4; wherein hybridization of the probe to the mRNA or cDNA in the sample indicates the presence of a PIK3C2G fusion polynucleotide in the mammal.

Hybridization, as described throughout the specification, may be carried out under stringent conditions, e.g., medium or high stringency. See, e.g., J. Sambrook, E. F. Fritsch, and T. Maniatis, *Molecular Cloning: A Laboratory Manual*, Cold Spring Harbor Laboratory Pr; 2nd edition (1989); T. Brown, *Hybridization Analysis of DNA Blots. Current Protocols in Molecular Biology* at 21:2.10.1-2.10.16 (2001). High stringency conditions for hybridization refer to conditions under which two nucleic acids must possess a high degree of base pair homology to each other in order to hybridize. Examples of highly stringent conditions for hybridization include hybridization in 4× sodium chloride/sodium citrate (SSC), at 65 or 70° C., or hybridization in 4×SSC plus 50% formamide at about 42 or 50° C., followed by at least one, at least two, or at least three washes in 1×SSC, at 65 or 70° C. Another example of highly stringent conditions includes hybridization in 2×SSC; 10×Denhardt solution (Fikoll 400+PEG+BSA; ratio 1:1:1); 0.1% SDS; 5 mM EDTA; 50 mM Na$_2$HPO$_4$; 250 µg/ml of herring sperm DNA; 50 µg/ml of tRNA; or 0.25 M of sodium phosphate buffer, pH 7.2; 1 mM EDTA7% SDS at 60° C.; followed by washing 2×SSC, 0.1% SDS at 60° C.

The nucleic acid fragments can be detectably labeled with, e.g., a radiolabel, a fluorescent label, a bioluminescent label, a chemiluminescent label, an enzyme label, a binding pair label (e.g., biotin/streptavidin), or can include an affinity tag or identifier (e.g., an adaptor, barcode or other sequence identifier). Labeled or unlabeled nucleic acids and/or nucleic acid fragments of the invention may be used in reagents for detecting, capturing, and/or isolating PIK3C2G gene fusions, such as, e.g. EFNA3:PIK3C2G (for example, all or part of SEQ ID NO: 1) or ERC1:PIK3C2G (for example, all or part of SEQ ID NO:3).

In some embodiments, the method comprises performing chromosome in situ hybridization with chromosomal DNA from a biological sample to detect the presence of a PIK3C2G gene fusion (such as, e.g., EFNA3:PIK3C2G or ERC1:PIK3C2G, as disclosed herein). In some embodiments, the chromosome in situ hybridization comprises the steps of: providing a chromosome (e.g., interphase or metaphase chromosome) preparation (e.g., by attaching the chromosomes to a substrate (e.g., glass)); denaturing the chromosomal DNA (e.g., by exposure to formamide) to separate the double strands of the polynucleotides from each other; exposing the nucleic acid probe to the chromosomes under conditions to allow hybridization of the probe to the target DNA; removing unhybridized or non-specifically hybridized probes by washing; and detecting the hybridization of the probe with the target DNA. In some embodiments, the chromosome in situ hybridization is fluorescence in situ hybridization (FISH). In some embodiments, the probe is labeled directly by a fluorescent label, or indirectly by incorporation of a nucleotide containing a tag or reporter molecule (e.g., biotin, digoxigenin, or hapten) which after hybridization to the target DNA is then bound by fluorescently labeled affinity molecule (e.g., an antibody or streptavidin). In some embodiments, the hybridization of the probe with the target DNA in FISH can be visualized using a fluorescence microscope.

In other embodiments, the method comprises performing Southern blot with DNA polynucleotides from a biological sample to detect the presence of an PIK3C2G gene fusion. In some embodiments, the Southern blot comprises the steps of: optionally fragmenting the polynucleotides into smaller sizes by restriction endonucleases; separating the polynucleotides by gel electrophoresis; denaturing the polynucleotides (e.g., by heat or alkali treatment) to separate the double strands of the polynucleotides from each other; transferring the polynucleotides from the gel to a membrane (e.g., a nylon or nitrocellulose membrane); immobilizing the polynucleotides to the membrane (e.g., by UV light or heat); exposing the nucleic acid probe to the polynucleotides under conditions to allow hybridization of the probe to the target DNA; removing unhybridized or non-specifically hybridized probes by washing; and detecting the hybridization of the probe with the target DNA.

Amplification-Based Assays

In certain embodiments, the method of detecting the presence of a PIK3C2G gene fusion, comprises (a) performing a PCR amplification reaction with polynucleotides from a biological sample, wherein the amplification reaction utilizes a pair of primers which will amplify at least a fragment of the PIK3C2G gene fusion, wherein the fragment comprises the fusion junction, wherein the first primer is in sense orientation and the second primer is in antisense orientation; and (b) detecting an amplification product, wherein the presence of the amplification product is indicative of the presence of a PIK3C2G fusion polynucleotide in the sample. In specific exemplary embodiments, the PIK3C2G gene fusion is EFNA3:PIK3C2G, such as, e.g., the gene fusion of SEQ ID NO: 1 or a fragment thereof, e.g., a nucleotide sequence comprising nucleotides 438-447, 433-452, 423-462, 393-492, 338-517, or 343-542 of SEQ ID NO:1. In other exemplary embodiments, the gene fusion is ERC1:PIK3C2G, such as, e.g., the gene fusion of SEQ ID NO:3 or a fragment thereof, e.g., a nucleotide sequence comprising nucleotides 2347-2356, 2342-2361, 2332-2371, 2302-2401, 2247-2426, or 2252-2451 of SEQ ID NO:3. In some embodiments, step (a) of performing a PCR amplification reaction comprises: (i) providing a reaction mixture comprising the polynucleotides (e.g., DNA or cDNA) from the biological sample, the pair of primers which will amplify at least a fragment of the PIK3C2G gene fusion wherein the first primer is complementary to a sequence on the first strand of the polynucleotides and the second primer is complementary to a sequence on the second strand of the polynucleotides, a DNA polymerase, and a plurality of free nucleotides comprising adenine, thymine, cytosine, and guanine (dNTPs); (ii) heating the reaction mixture to a first predetermined temperature for a first predetermined time to separate the double strands of the polynucleotides from each other; (iii) cooling the reaction mixture to a second predetermined temperature for a second predetermined time under conditions to allow the first and second primers to hybridize with their complementary sequences on the first and second strands of the polynucleotides, and to allow the DNA polymerase to extend the primers; and (iv) repeating steps (ii) and (iii) for a predetermined number of cycles (e.g., 10, 15, 20, 25, 30, 35, 40, 45, or 50 cycles). In some embodiments, the polynucleotides from the biological sample comprise RNA, and the method further comprises performing a RT-PCR amplification reaction with the RNA to synthesize cDNA as the template for subsequent or simultaneous PCR reactions. In some embodiments, the RT-PCR amplification reaction comprises providing a reaction mixture comprising the RNA, a primer which will amplify the RNA (e.g., a sequence-specific primer, a random primer, or oligo(dT)s), a reverse transcriptase, and dNTPs, and heating the reaction mixture to a third predetermined temperature for a third predetermined time under conditions to allow the reverse transcriptase to extend the primer.

Sequencing and Genotyping

Another method for determining the presence of a PIK3C2G gene fusion molecule (such as, e.g., EFNA3:PIK3C2G or ERC1:PIK3C2G, as disclosed herein) includes: sequencing a portion of the nucleic acid molecule (e.g., sequencing the portion of the nucleic acid molecule that comprises the fusion junction of a PIK3C2G gene fusion), thereby determining that the PIK3C2G gene fusion is present in the nucleic acid molecule. In some exemplary embodiments, the gene fusion is EFNA3:PIK3C2G. In other exemplary embodiments, the gene fusion is ERC1:PIK3C2G. Optionally, the sequence acquired is compared to a reference sequence, or a wild type reference sequence. In one embodiment, the sequence is determined by a next generation sequencing method. In some embodiments, the sequencing is automated and/or high-throughput sequencing. The method can further include acquiring, e.g., directly or indirectly acquiring, a sample, e.g., a tumor or cancer sample, from a patient.

In some embodiments, the sequencing comprises chain terminator sequencing (Sanger sequencing), comprising: providing a reaction mixture comprising a nucleic acid molecule from a biological sample, a primer complementary to a region of the template nucleic acid molecule, a DNA polymerase, a plurality of free nucleotides comprising adenine, thymine, cytosine, and guanine (dNTPs), and at least one chain terminating nucleotide (e.g., at least one di-deoxynucleotide (ddNTPs) chosen from ddATP, ddTTP, ddCTP, and ddGTP), wherein the at least one chain terminating nucleotide is present in a low concentration so that chain termination occurs randomly at any one of the positions containing the corresponding base on the DNA strand; annealing the primer to a single strand of the nucleic acid molecule; extending the primer to allow incorporation of the chain terminating nucleotide by the DNA polymerase to produce a series of DNA fragments that are terminated at positions where that particular nucleotide is used; separating the polynucleotides by electrophoresis (e.g., gel or capillary electrophoresis); and determining the nucleotide order of the template nucleic acid molecule based on the positions of chain termination on the DNA fragments. In some embodiments, the sequencing is carried out with four separate base-specific reactions, wherein the primer or the chain terminating nucleotide in each reaction is labeled with a separate fluorescent label. In other embodiments, the sequencing is carried out in a single reaction, wherein the four chain terminating nucleotides mixed in the single reaction are each labeled with a separate fluorescent label.

In some embodiments, the sequencing comprises pyrosequencing (sequencing by synthesis), comprising: (i) providing a reaction mixture comprising a nucleic acid molecule from a biological sample, a primer complementary to a region of the template nucleic acid molecule, a DNA polymerase, a first enzyme capable of converting pyrophosphate into ATP, and a second enzyme capable using ATP to generates a detectable signal (e.g., a chemiluminescent signal, such as light) in an amount that is proportional to the amount of ATP; (ii) annealing the primer to a single strand of the nucleic acid molecule; (iii) adding one of the four free nucleotides (dNTPs) to allow incorporation of the correct, complementary dNTP onto the template by the DNA polymerase and release of pyrophosphate stoichiometrically; (iv) converting the released pyrophosphate to ATP by the first enzyme; (v) generating a detectable signal by the second enzyme using the ATP; (vi) detecting the generated signal and analyzing the amount of signal generated in a pyrogram; (vii) removing the unincorporated nucleotides; and (viii) repeating steps (iii) to (vii). The method allows sequencing of a single strand of DNA, one base pair at a time, and detecting which base was actually added at each step. The solutions of each type of nucleotides are sequentially added and removed from the reaction. Light is produced only when the nucleotide solution complements the first unpaired base of the template. The order of solutions which produce detectable signals allows the determination of the sequence of the template.

In some embodiments, the method of determining the presence of a PIK3C2G fusion (such as, e.g., EFNA3:PIK3C2G or ERC1:PIK3C2G, as disclosed herein) comprises analyzing a nucleic acid sample (e.g., DNA, cDNA, or RNA, or an amplification product thereof) by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of a PIK3C2G fusion (such as, e.g., EFNA3:PIK3C2G or ERC1:PIK3C2G, as disclosed herein) comprises analyzing a nucleic acid sample (e.g., DNA, cDNA, or RNA, or an amplification product thereof) by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

Methods for Detecting Fusion Proteins

Another aspect of the invention provides a method of determining the presence of a PIK3C2G fusion protein (such as, e.g., EFNA3:PIK3C2G or ERC1:PIK3C2G, as disclosed herein) in a mammal. The method comprises the steps of obtaining a biological sample of a mammal (such as, e.g., from a human cancer), and exposing that sample to at least one reagent that detects a PIK3C2G fusion protein (e.g., an antibody that recognizes the PIK3C2G fusion but does not recognize the wild type PIK3C2G or the wild type fusion partner) to determine whether a PIK3C2G fusion protein is present in the biological sample. The detection of a PIK3C2G fusion protein indicates the presence of a mutant PIK3C2G in the mammal (such as, e.g., in the human cancer). In some embodiments, the PIK3C2G fusion protein comprises an amino acid sequence having at least 85%, at least 90%, at least 95%, at least 97%, or at least 98% identity with an amino acid sequence of SEQ ID NO:2 or SEQ ID NO:4. In some embodiments the human cancer is breast cancer. In some embodiments, the reagent that detects a PIK3C2G fusion protein can be detectably labeled with, e.g., a radiolabel, a fluorescent label, a bioluminescent label, a chemiluminescent label, an enzyme label, a binding pair label (e.g., biotin/streptavidin), an antigen label, or can include an affinity tag or identifier (e.g., an adaptor, barcode or other sequence identifier). In some embodiments, the labeled reagent can be detected using, e.g., autoradiography, microscopy (e.g., brightfield, fluorescence, or electron microscopy), ELISA, or immunohistochemistry. In some embodiments, the PIK3C2G protein fusion is detected in a biological sample by a method chosen from one or more of: antibody-based detection (e.g., western blot, ELISA, immunohistochemistry) size-based detection methods (e.g., HPLC or mass spectrometry), or protein sequencing.

Antibody-Based Detection

In some embodiments, the method comprises performing western blot with polypeptides from a biological sample to detect the presence of a PIK3C2G fusion protein (such as, e.g., EFNA3:PIK3C2G or ERC1:PIK3C2G, as disclosed herein). In some embodiments, the western blot comprises the steps of: separating the polypeptides by gel electrophoresis; transferring the polypeptides from the gel to a membrane (e.g., a nitrocellulose or polyvinylidene difluoride (PVDF) membrane); blocking the membrane to prevent nonspecific binding by incubating the membrane in a dilute solution of protein (e.g., 3-5% bovine serum albumin (BSA) or non-fat dry milk in Tris-Buffered Saline (TBS) or I-Block, with a minute percentage (e.g., 0.1%) of detergent, such as, e.g., Tween 20 or Triton X-100); exposing the polypeptides to at least one reagent that detects a PIK3C2G fusion protein (e.g., an antibody that recognizes the PIK3C2G fusion but does not recognize the wild type PIK3C2G or the wild type fusion partner); removing unbound or non-specifically bound reagent by washing; and detecting the binding of the reagent with the target protein. In some embodiments, the method comprises two-step detection: exposing the polypeptides to a primary antibody that specifically binds to a PIK3C2G fusion protein; removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the reagent that detects a PIK3C2G fusion protein (e.g., the fusion specific antibody, or the secondary antibody) is directly labeled for detection. In other embodiments, the reagent is linked to an enzyme, and the method further comprises adding a substrate of the enzyme to the membrane; and developing the membrane by detecting a detectable signal produced by the reaction between the enzyme and the substrate. For example, the reagent may be linked with horseradish peroxidase to cleave a chemiluminescent agent as a substrate, producing luminescence in proportion to the amount of the target protein for detection.

In some embodiments, the method comprises performing ELISA with polypeptides from a biological sample to detect the presence of a PIK3C2G fusion protein (such as, e.g., EFNA3:PIK3C2G or ERC1:PIK3C2G, as disclosed herein). In some embodiments, the ELISA is chosen from, e.g., direct ELISA, indirect ELISA, sandwich ELISA, and competitive ELISA.

In one embodiment, the direct ELISA comprises the steps of: attaching polypeptides from a biological sample to a surface; blocking the surface to prevent nonspecific binding by incubating the surface in a dilute solution of protein; exposing the polypeptides to an antibody that specifically binds to a PIK3C2G fusion protein (e.g., an antibody that recognizes the PIK3C2G fusion (such as, e.g., EFNA3:PIK3C2G or ERC1:PIK3C2G, as disclosed herein) but does not recognize the wild type PIK3C2G or the wild type fusion partner); removing unbound or non-specifically bound antibody by washing; and detecting the binding of the antibody with the target protein. In some embodiments, the antibody is directly labeled for detection. In other embodiments, the antibody is linked to an enzyme, and the method further comprises adding a substrate of the enzyme; and detecting a detectable signal produced by the reaction between the enzyme and the substrate.

In another embodiment, the indirect ELISA comprises the steps of: attaching polypeptides from a biological sample to a surface; blocking the surface to prevent nonspecific binding by incubating the surface in a dilute solution of protein; exposing the polypeptides to a primary antibody that specifically binds to a PIK3C2G fusion protein (such as, e.g., EFNA3:PIK3C2G or ERC1:PIK3C2G, as disclosed herein); removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the secondary antibody is directly labeled for detection. In other embodiments, the secondary antibody is linked to an enzyme, and the method further comprises adding a substrate of the enzyme; and detecting a detectable signal produced by the reaction between the enzyme and the substrate.

In some embodiments, the method comprises performing immunohistochemistry with polypeptides from a biological sample to detect the presence of a PIK3C2G fusion protein (such as, e.g., EFNA3:PIK3C2G or ERC1:PIK3C2G, as disclosed herein). In some embodiments, the immunohistochemistry comprises the steps of: fixing a cell or a tissue section (e.g., by paraformaldehyde or formalin treatment); permeabilizing the cell or tissue section to allow target accessibility; blocking the cell or tissue section to prevent nonspecific binding; exposing the cell or tissue section to at least one reagent that detects a PIK3C2G fusion protein (e.g., an antibody that recognizes the PIK3C2G fusion but does not recognize the wild type PIK3C2G or the wild type fusion partner); removing unbound or non-specifically bound reagent by washing; and detecting the binding of the reagent with the target protein. In some embodiments, the reagent is directly labeled for detection. In other embodiments, the reagent is linked to an enzyme, and the method further comprises adding a substrate of the enzyme; and detecting a detectable signal produced by the reaction between the enzyme and the substrate. In some embodiments, the immunohistochemistry may comprise the two-step detection as in the indirect ELISA.

Size-Based Detection Methods

In some embodiments, the method of determining the presence of a PIK3C2G fusion (such as, e.g., EFNA3:PIK3C2G or ERC1:PIK3C2G, as disclosed herein) comprises analyzing a protein sample by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of a PIK3C2G fusion (such as, e.g., EFNA3:PIK3C2G or ERC1:PIK3C2G, as disclosed herein) comprises analyzing a protein sample by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

Detection of a PIK3C2G gene fusion or a PIK3C2G fusion protein in a patient can lead to assignment of the patient to the newly identified patient population that bears the PIK3C2G fusion. Because this patient population can suffer from or be susceptible to a disorder associated with an aberrant PIK3C2G expression or activity, or overexpression of PIK3C2G, detection of the PIK3C2G fusion can also lead to diagnosis of such disorder. Thus, a further aspect of the invention provides a method of stratifying a patient population (e.g., assigning a patient to a group or class) and/or diagnosing a patient, comprising: obtaining a biological sample from the patient, contacting the sample to at least one reagent that detects a PIK3C2G gene fusion or a PIK3C2G fusion protein to determine whether a PIK3C2G fusion is present in the biological sample. The detection of a PIK3C2G fusion indicates that the patient belongs to the newly identified patient population that bears the PIK3C2G fusion, and/or the presence of a disorder associated with aberrant PIK3C2G expression or activity, or overexpression of PIK3C2G, such as, e.g., a cancer. The detection of a PIK3C2G fusion also identifies a new subtype of cancer, which is characterized by the presence of the PIK3C2G fusion, such as, e.g., certain breast cancers. In certain embodiments, the PIK3C2G fusion is EFNA3:PIK3C2G. In some embodiments, the EFNA3:PIK3C2G fusion comprises all or part of the nucleotide and/or amino acid sequence (such as, e.g., the fusion junction) set forth in SEQ ID NO:1 and SEQ ID NO:2, respectively. In other embodiments, the PIK3C2G fusion is ERC1:PIK3C2G. In some embodiment the ERC1:PIK3C2G fusion comprises all or a part of the nucleotide and/or amino acid sequence (such as, e.g., the fusion junction) set forth in SEQ ID NO:3 and SEQ ID NO:4, respectively.

In some embodiments, the PIK3C2G gene fusion or PIK3C2G fusion protein is detected prior to initiating, during, and/or after, a treatment of a patient with, e.g., a PIK3C2G inhibitor (such as, e.g., a kinase inhibitor) or a PIK3C2G fusion inhibitor. In one embodiment, the PIK3C2G gene fusion or PIK3C2G fusion protein is detected at the time the patient is diagnosed with a cancer. In other embodiment, the PIK3C2G fusion is detected at a pre-determined interval, e.g., a first point in time and at least at a subsequent point in time. In certain embodiments, in response to detection of a PIK3C2G fusion, such as, e.g., EFNA3:PIK3C2G or ERC1:PIK3C2G, the method further includes one or more of:

(1) stratifying a patient population (e.g., assigning a patient, to a group or class);

(2) identifying or selecting the patient as likely or unlikely to respond to a treatment, e.g., a kinase inhibitor treatment, a PIK3C2G inhibitor treatment, or a PIK3C2G fusion inhibitor treatment as described herein;

(3) selecting a treatment regimen, e.g., administering or not administering a preselected therapeutic agent, such as, e.g., a PIK3C2G inhibitor or a PIK3C2G fusion inhibitor;

(4) prognosticating the time course of the disease in the patient (e.g., evaluating the likelihood of increased or decreased patient survival); or (5) monitoring the effectiveness of treatment (e.g., by detecting a reduction in the level of PIK3C2G gene fusion or fusion protein in a patient sample).

In certain embodiments, upon detection of a PIK3C2G gene fusion or PIK3C2G fusion protein in a patient's biological sample, the patient is identified as likely to respond to a treatment that comprises a PIK3C2G inhibitor. In some embodiments, the PIK3C2G fusion detected is an EFNA3:PIK3C2G fusion. In alternate embodiments, the PIK3C2G fusion detected is an ERC1:PIK3C2G fusion.

A further aspect of the invention provides a method of selecting a treatment option by detecting a PIK3C2G fusion. The method comprises obtaining a biological sample from a patient and exposing the sample to at least one reagent that detects a PIK3C2G gene fusion or fusion protein to determine whether a PIK3C2G fusion is present in the biological sample. The detection of the PIK3C2G gene fusion or fusion protein indicates the likelihood of the patient responding to treatment with a PIK3C2G inhibitor or a PIK3C2G fusion inhibitor. The method may be augmented or personalized by evaluating the effect of a variety of PIK3C2G or PIK3C2G fusion inhibitors on the biological sample shown to contain a PIK3C2G gene fusion or fusion protein to determine the most appropriate inhibitor to administer. In some embodiments, the PIK3C2G fusion detected is an EFNA3:PIK3C2G fusion. In some embodiments, the EFNA3:PIK3C2G fusion comprises all or a part of the nucleotide and/or amino acid sequence (such as, e.g., the fusion junction) set forth in SEQ ID NO:1 and SEQ ID NO:2, respectively. In alternate embodiments, the PIK3C2G fusion detected is an ERC1:PIK3C2G fusion. In some embodiments, the ERC1:PIK3C2G fusion comprises all or a part of the nucleotide and/or amino acid sequence (such as, e.g., the fusion junction) set forth in SEQ ID NO:3 and SEQ ID NO:4, respectively.

Methods of Treatment

Alternatively, or in combination with the detection and diagnostic methods described herein, the invention provides method for treating the newly identified patient population and the new PIK3C2G fusion cancer subtype, which are characterized by the presence of a PIK3C2G fusion. The patient population and cancer subtype can be associated with or predict the onset of a condition mediated by aberrant PIK3C2G expression or activity, or overexpression of PIK3C2G, such as, e.g., a cancer or a tumor harboring a PIK3C2G fusion. In certain embodiments, the cancer or tumor harboring a PIK3C2G fusion is breast cancer. The methods comprise administering a therapeutic agent, e.g., a PIK3C2G inhibitor (such as e.g., a kinase inhibitor, an antibody specific to PIK3C2G); or a PIK3C2G fusion inhibitor, i.e., an inhibitor that blocks the activity of the PIK3C2G fusion but not wild type PIK3C2G or wild type fusion partner (such as, e.g., an antibody specific to an EFNA3:PIK3C2G or ERC1:PIK3C2G fusion protein, or any one of the antibodies described above; or an RNA inhibitor that recognizes PIK3C2G or the fusion junction of a PIK3C2G gene fusion, including but not limited to siRNA, dsRNA, shRNA, or any other antisense nucleic acid inhibitor), alone or in combination with e.g., other chemotherapeutic agents or procedures, in an amount sufficient to treat a condition mediated by aberrant PIK3C2G expression or activity, or overexpression of PIK3C2G by one or more of the following: e.g., impeding growth of a cancer, causing a cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

In certain embodiments, the PIK3C2G fusion proteins of the invention may be inhibited by a PIK3C2G inhibitor or a PIK3C2G fusion inhibitor. In some embodiments, the therapeutic agent is a PIK3C2G inhibitor, such as, e.g., a compound, biological or chemical, which inhibits, directly or indirectly, the expression and/or activity of PIK3C2G. For example, the PIK3C2G inhibitors may be an antibody (such as, e.g., antibodies specific to PIK3C2G) or a small molecule inhibitor. In some embodiments, the inhibitors may act directly on PIK3C2G itself, modify the activity of PIK3C2G, or inhibit the expression of PIK3C2G. In other embodiments, the inhibitors may indirectly inhibit PIK3C2G activity by inhibiting the activity of proteins or molecules other than PIK3C2G itself. For example, the inhibitors may modulate the activity of regulatory kinases that phosphorylate or dephosphorylate PIK3C2G, interfere with binding of ligands, or inhibit the activity of interacting or downstream proteins or molecules.

Exemplary small molecule inhibitors include pan-kinase inhibitors with activity against several different kinases (including PIK3C2G) or specific inhibitors (i.e., inhibitors specific to PIK3C2G). In one embodiment, the PIK3C2G fusion protein, such as, e.g., an EFNA3:PIK3C2G fusion protein or an ERC1:PIK3C2G fusion protein, is inhibited by a kinase inhibitor, such as the compound shown below.

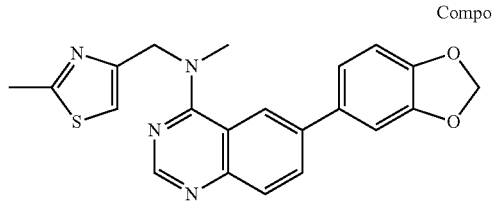

Compound 1

(see A. Rosenthal et al., *Bioorg Med Chem Lett.*; 21(10): 3152-3158 (2011)).

In some embodiments, the PIK3C2G fusion protein is inhibited by a PIK3C2G fusion inhibitor, such as, e.g., an antibody that recognizes all or part of a PIK3C2G fusion (such as, e.g., an EFNA3:PIK3C2G fusion protein or an ERC1:PIK3C2G fusion protein) but does not recognize wild type PIK3C2G or wild type fusion partner (such as, e.g., EFNA3 or ERC1). In some embodiments, the PIK3C2G fusion protein (such as, e.g., an EFNA3:PIK3C2G fusion protein or an ERC1:PIK3C2G fusion protein) is inhibited by an agent that inhibits transcription or translation of the fusion protein, e.g., an RNA inhibitor that recognizes the PIK3C2G coding sequence, the binding partner (e.g., EFNA3 or ERC1), or the binding partner: PIK3C2G fusion junction, including but not limited to small interfering RNA (siRNA), double stranded RNA (dsRNA), short-hairpin RNA (shRNA), or any other antisense nucleic acid inhibitor. In some embodiments, the PIK3C2G fusion inhibited is selected from all or a portion of SEQ ID NO: 1, SEQ ID NO:2, SEQ ID NO:3, or SEQ ID NO:4

As used herein, and unless otherwise specified, a "therapeutically effective amount" of a compound is an amount sufficient to provide a therapeutic benefit in the treatment or management of a condition mediated by aberrant PIK3C2G expression or activity, or overexpression of PIK3C2G, such as, delaying or minimizing one or more symptoms associated with a cancer or a tumor harboring a PIK3C2G fusion (such as, e.g., EFNA3:PIK3C2G or ERC1:PIK3C2G, as disclosed herein). A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the condition mediated by aberrant PIK3C2G expression or activity, or overexpression of PIK3C2G, or enhances the therapeutic efficacy of another therapeutic agent.

In some embodiments, the patient to be treated is suffering from breast cancer, and the method for treating the condition comprises administering to the patient a therapeutically effective amount of a PIK3C2G inhibitor or a PIK3C2G fusion inhibitor.

In some embodiments, the patient to be treated is suffering from breast cancer, and the method for treating the condition comprises administering to the patient a therapeutically effective amount of a PIK3C2G3-specific inhibitor.

Screening Methods

Therapeutic agents, such as e.g., PIK3C2G inhibitors or PIK3C2G fusion inhibitors, used in the therapeutic methods of the invention can be evaluated using the screening assays described herein. Thus, the invention provides a method of identifying an agent useful for treating a condition mediated by aberrant PIK3C2G expression or activity, or overexpression of PIK3C2G, such as, e.g., cancer or a tumor harboring a PIK3C2G fusion, such as e.g., breast cancer, comprising contacting a cell expressing a PIK3C2G gene fusion or PIK3C2G fusion protein with a candidate agent and determining whether the expression level of the fusion is decreased or a biological function associated with the fusion is altered. In one embodiment, therapeutic agents can be evaluated in a cell-free system, e.g., a cell lysate or in a reconstituted system. In other embodiments, the therapeutic agents are evaluated in a cell in culture, e.g., a cell expressing a PIK3C2G fusion (e.g., a mammalian cell, a tumor cell or cell line, a recombinant cell). In yet other embodiments, the therapeutic agents are evaluated in a cell in vivo (e.g., a PIK3C2G fusion-expressing cell present in a subject, e.g., an animal subject (e.g., an in vivo animal model)).

Exemplary parameters to evaluate in determining the efficacy of a therapeutic agent for treating a condition mediated by aberrant PIK3C2G expression or activity, or overexpression of PIK3C2G, such as, e.g., a cancer or a tumor harboring a PIK3C2G fusion include one or more of:

(i) a change in binding activity, e.g., direct binding of the candidate agent to a PIK3C2G fusion protein; or a binding competition between a known ligand and the candidate agent to a PIK3C2G fusion protein;

(ii) a change in kinase activity, e.g., phosphorylation levels of a PIK3C2G fusion protein (e.g., an increased or decreased phosphorylation or autophosphorylation); or a change in phosphorylation of a target of a PIK3C2G kinase—in certain embodiments, a change in kinase activity, e.g., phosphorylation, is detected by any of western blot (e.g., using an anti-PIK3C2G antibody or a phosphor-specific antibody, detecting a shift in the molecular weight of a PIK3C2G fusion protein), mass spectrometry, immunoprecipitation, immunohistochemistry, immunomagnetic beads, among others;

(iii) a change in an activity of a cell containing a PIK3C2G fusion (e.g., a tumor cell or a recombinant cell), e.g., a change in proliferation, morphology, or tumorigenicity of the cell;

(iv) a change in tumor present in an animal subject, e.g., size, appearance, or proliferation of the tumor; or (v) a change in the level, e.g., expression level (transcription and/or translation) of a PIK3C2G fusion protein or nucleic acid molecule; or (vi) a change in an activity of a signaling pathway involving PIK3C2G, e.g., phosphorylation or activity of a interacting or downstream target, or expression level of a target gene.

In some embodiments, the PIK3C2G fusion is an EFNA3:PIK3C2G fusion or an ERC1:PIK3C2G fusion.

In one embodiment, a change in the activity of a PIK3C2G fusion, or interaction of a PIK3C2G fusion with a downstream ligand detected in a cell free assay in the presence of a candidate agent indicates that the candidate agent will be effective as a therapeutic agent for treatment of a condition mediated by aberrant PIK3C2G expression or activity, or overexpression of PIK3C2G, such as, e.g., a cancer or a tumor harboring a PIK3C2G fusion (such as, e.g., breast cancer).

In other embodiments, a change in an activity of a cell expressing a PIK3C2G fusion, such as, e.g., EFNA3:PIK3C2G or ERC1:PIK3C2G, as disclosed herein, (e.g., a mammalian cell, a tumor cell or cell line, a recombinant cell) is detected in a cell in culture. In one embodiment, the cell is a recombinant cell that is modified to express a PIK3C2G fusion nucleic acid, e.g., is a recombinant cell transfected with a PIK3C2G fusion nucleic acid. The transfected cell can show a change in response to the expressed PIK3C2G fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a PIK3C2G fusion. In other embodiments, a change in binding activity or phosphorylation of PIK3C2G or its interacting or downstream proteins or molecules as described herein is detected.

In yet other embodiment, a change in a tumor present in an animal subject (e.g., an in vivo animal model) is detected. In one embodiment, a tumor containing animal or a xenograft comprising cells expressing a PIK3C2G fusion (e.g., tumorigenic cells expressing a PIK3C2G fusion) is employed. The therapeutic agents can be administered to the animal subject and a change in the tumor is evaluated. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor or modulator.

In another aspect of the invention provides a method or assay for screening for agents that modulate (e.g., inhibit) the expression or activity of a PIK3C2G fusion as described herein. The method includes contacting e.g., a PIK3C2G fusion, or a cell expressing a PIK3C2G fusion, with a candidate agent; and detecting a change in a parameter associated with a PIK3C2G fusion, e.g., a change in the expression or an activity of the PIK3C2G fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the PIK3C2G fusion is detected, the candidate agent is identified as an inhibitor. In another embodiment, if an increase in expression or activity of the PIK3C2G fusion is detected, the candidate agent is identified as an activator. In certain embodiments, the PIK3C2G fusion is a PIK3C2G gene fusion or PIK3C2G fusion protein, where in the fusion is e.g., an EFNA3: PIK3C2G fusion or an ERC1:PIK3C2G fusion.

In one embodiment, the contacting step is detected in a cell-free system, e.g., a cell lysate or in a reconstituted system. In other embodiments, the contacting step is detected in a cell in culture, e.g., a cell expressing a PIK3C2G fusion (e.g., a mammalian cell, a tumor cell or cell line, a recombinant cell). In yet other embodiments, the contacting step is detected in a cell in vivo (a PIK3C2G expressing cell present in a subject, e.g., an animal subject (e.g., an in vivo animal model)).

Exemplary parameters evaluated in identifying an agent that modulates the activity of a PIK3C2G fusion, e.g., a PIK3C2G fusion (e.g., an EFNA3:PIK3C2G fusion or an ERC1:PIK3C2G fusion) include one or more of:

(i) a change in binding activity, e.g., direct binding of the candidate agent to a PIK3C2G fusion protein; a binding competition between a known ligand and the candidate agent to a PIK3C2G fusion protein;

(ii) a change in kinase activity, e.g., phosphorylation levels of a PIK3C2G fusion protein (e.g., an increased or decreased phosphorylation or autophosphorylation); or a change in phosphorylation of a target of a PIK3C2G kinase—in certain embodiments, a change in kinase activity, e.g., phosphorylation, is detected by any of Western blot (e.g., using an anti-PIK3C2G antibody; a phosphor-specific antibody, detecting a shift in the molecular weight of a PIK3C2G fusion protein), mass spectrometry, immunoprecipitation, immunohistochemistry, immunomagnetic beads, among others;

(iii) a change in an activity of a cell containing a PIK3C2G fusion (e.g., a tumor cell or a recombinant cell), e.g., a change in proliferation, morphology, or tumorigenicity of the cell;

(iv) a change in tumor present in an animal subject, e.g., size, appearance, or proliferation of the tumor;

(v) a change in the level, e.g., expression level (transcription and/or translation) of a PIK3C2G fusion protein or nucleic acid molecule; or (vi) a change in an activity of a signaling pathway involving PIK3C2G, e.g., phosphorylation or activity of a interacting or downstream target, or expression level of a target gene.

Methods for Validating PIK3C2G Fusions

PIK3C2G gene fusions, such as, e.g., EFNA3:PIK3C2G gene fusions or ERC1:PIK3C2G gene fusions, may be evaluated to ensure that the breakpoints are in-frame and can produce a protein product containing the full kinase domain, i.e., that the breakpoint occurs such that complete triplet codons are intact, and that the RNA sequence will produce a viable protein. The PIK3C2G gene fusion can be transfected into cells to confirm that the protein is functionally active with respect to kinase activity and oncogenic activity. cDNA encoding the PIK3C2G fusion protein can be produced by standard solid-phase DNA synthesis. Alternatively the PIK3C2G fusion cDNA can be produced by RT-PCR using tumor mRNA extracted from samples containing the gene fusion. The DNA amplified can be subcloned into an appropriate vector and characterized by DNA sequence analysis or in vitro/in vivo expression analyses.

Expression vectors containing the PIK3C2G gene fusion (such as, e.g., an EFNA3:PIK3C2G gene fusion or an ERC1:PIK3C2G gene fusion) can be introduced into host cells to thereby produce a PIK3C2G fusion protein (such as, e.g., an EFNA3:PIK3C2G fusion protein or an ERC1: PIK3C2G fusion protein). The PIK3C2G fusion protein expression vector can be a yeast expression vector, a vector for expression in insect cells, e.g., a baculovirus expression vector, or a vector suitable for expression in mammalian cells. Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell.

Cells harboring the expression vector carrying the recombinant PIK3C2G gene fusion can then be tested for production of the unique fusion protein via standard western blotting using either an antibody probe that detects the gene product itself or that recognizes a tag peptide (e.g., FLAG tag) that can be added to the gene product via the expression vector (using standard, commercially available reagents). Western blotting can be used to confirm the ectopic expression of the encoded PIK3C2G fusion protein by comparing the samples from cells transfected with the vector containing the PIK3C2G gene fusion cDNA to cells transfected with the empty expression vector. The functional activity can be assessed by measuring the level of phosphorylation on the kinase or substrate. Comparison of the level of phosphorylation activity between the wild type (normal) form of PIK3C2G and the PIK3C2G fusion protein can indicate if the PIK3C2G fusion protein has elevated activity that could drive oncogenic activity. Whether the PIK3C2G gene fusion is oncogenic can be assessed by measuring capacity of the expressed PIK3C2G fusion protein to transform cells, that is, to enable cells to grow and proliferate under conditions which are not permissive for growth of normal cells. One commonly used method of measuring the transforming activity of a kinase is by assessing if expression of the gene product can allow BaF3 cells to grow in the absence of the growth factor IL3, which is required for the survival and growth of BaF3 cells. Another assay for measuring transforming activity is a soft agar growth assay. This is another standard method which tests the capacity of an introduced gene product to confer the ability to grow in a soft agar matrix, or anchorage-independent conditions. These methods and others can be used to test the oncogenic activity of a PIK3C2G gene fusion (such as, e.g., an EFNA3:PIK3C2G gene fusion or an ERC1:PIK3C2G gene fusion) and provide a level of validation of a PIK3C2G fusion protein (such as, e.g., an EFNA3:PIK3C2G fusion protein or an ERC1:PIK3C2G fusion protein) as a potential target for treating patients that harbor these fusions.

A change in an activity of a cell can be detected in a cell in culture, e.g., a cell expressing a fusion (e.g., a mammalian cell, a tumor cell or cell line, a recombinant cell). The transfected cell can show a change in response to the expressed fusion, e.g., increased proliferation, changes in morphology, increased tumorigenicity, and/or an acquired transformed phenotype.

To further validate the biological implication of the gene fusion, a change in any of the activities of the cell, e.g., the recombinant cell, in the presence of a known inhibitor of one of the fusion partners, e.g., a PIK3C2G inhibitor, can be detected. For example, a decrease in one or more of: e.g., proliferation, tumorigenicity, or transformed morphology, in the presence of the PIK3C2G inhibitor can be indicative of an inhibitor of a fusion. In other embodiments, a change in binding activity or phosphorylation is detected.

All publications and patents mentioned herein are hereby incorporated by reference in their entirety as if each individual publication or patent was specifically and individually indicated to be incorporated by reference. To the extent publications and patents or patent applications incorporated by reference contradict the disclosure contained in the specification, the specification will supersede any contradictory material. Unless otherwise required by context, singular terms shall include the plural and plural terms shall include the singular. The use of "or" means "and/or" unless stated otherwise. The use of the term "including," as well as other forms, such as "includes" and "included," is not limiting. All ranges given in the application encompass the endpoints unless stated otherwise.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for detecting the presence of a PIK3C2G fusion selected from an EFNA3:PIK3C2G fusion and an ERC1:PIK3C2G fusion in a patient, said method comprising:
    a) contacting a biological sample from the patient with an oligonucleotide that hybridizes to the fusion junction of the PIK3C2G fusion, and detecting binding between the PIK3C2G fusion and the oligonucleotide; or
    b) amplifying or sequencing a portion of a nucleic acid from a biological sample from the patient, and detecting the presence of a nucleotide sequence comprising at least the fusion junction of the PIK3C2G fusion.

2. The method of claim 1, wherein the PIK3C2G fusion to be detected is a PIK3C2G gene fusion that comprises SEQ ID NOs:1 or 3, or a portion of SEQ ID NOs:1 or 3 comprising the fusion junction.

3. The method of claim 1, wherein the oligonucleotide hybridizes under stringent conditions to
    (a) a fragment of SEQ ID NO:1 comprising at least nucleotides 438-447 of SEQ ID NO:1; or
    (b) a fragment of SEQ ID NO:3 comprising at least nucleotides 2347-2356 of SEQ ID NO:3.

4. The method of claim 2, wherein the patient is suffering from or susceptible to a cancer.

5. The method of claim 4, wherein the cancer is breast cancer.

* * * * *

SEQUENCE LISTING

```
<160> NUMBER OF SEQ ID NOS: 4

<210> SEQ ID NO 1
<211> LENGTH: 3351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
atggcggcgg ctccgctgct gctgctgctg ctgctcgtgc ccgtgccgct gctgccgctg        60
ctggcccaag ggcccggagg ggcgctggga aaccggcatg cggtgtactg gaacagctcc       120
aaccagcacc tgcggcgaga gggctacacc gtgcaggtga acgtgaacga ctatctggat       180
atttactgcc cgcactacaa cagctcgggg gtgggccccg gggcgggacc ggggcccgga       240
ggcggggcag agcagtacgt gctgtacatg gtgagccgca acggctaccg cacctgcaac       300
gccagccagg gcttcaagcg ctgggagtgc aaccggccgc acgccccgca cagccccatc       360
aagttctcgg agaagttcca gcgctacagc gccttctctc tgggctacga gttccacgcc       420
ggccacgagt actactacat ctgcttgata gagaaggtaa caactgaact atccacatcc       480
atctaccagc taatcaatgt ctactgtaac agctttttatg cagattttca gcctgtaaat       540
gtacctagat gcacttccta tctaaatccc gggcttcctt cccacctcag cttcacagtg       600
tatgcagcac acaacattcc agaaacctgg gtgcacagga tcaatttttcc ccttgaaata       660 aagtcacttc caagggaatc catgctcact gtaaaactgt ttgggattgc ctgtgcaacc       720
```

```
aacaatgcaa atttactggc gtggacttgt cttccactgt ttccaaaaga aaaatccatt     780
ctcgggtcta tgctgttcag catgacatta cagagtgagc ctcccgtaga aatgataact     840
ccaggagtgt gggatgtaag tcagccatcc ccggtgaccc tgcagattga ttttccagct     900
actgggtggg agtatatgaa acctgattct gaagagaata gaagtaatct tgaagagcca     960
ctaaaggagt gtataaaaca tattgccaga cttttcacaga aacagactcc cctactactc    1020
tctgaagaaa agaaaagata tttatggttt tatcgcttct actgcaataa tgaaaactgc    1080
tcccttcctt tagtcctggg tagtgcccct ggatgggatg aaaggactgt ttcagaaatg    1140
cataccattt tgagaagatg gacatttct caacctttag aggctcttgg gcttttgact    1200
tccagttttc cagatcaaga aattcgtaaa gtggcagttc aacaattaga caacctcttg    1260
aatgatgaac tactggaata tctcccacag ctagttcagg ctgtcaagtt tgaatggaac    1320
cttgagagtc ctttagtgca acttctactc caccgctcct tgcagagcat ccaggttgcc    1380
catcgtcttt actggctgct aaaaaatgca gaaaatgaag cttattttaa aagctggtat    1440
cagaagctac tagctgctct ccaattctgt gcaggtaaag ccttgaatga tgagttttcc    1500
aaggagcaga aacttatcaa aattctggga gatattgggg aaagagtcaa gtctgccagt    1560
gaccatcaaa gacaggaggt actgaagaaa gaaattggca gactagaaga gttcttttcaa   1620
gatgtaaata cttgtcatct tcctctgaac cctgccctat gtataaaagg gattgatcac    1680
gatgcatgtt catattttac atctaatgct ttgccattga agattacttt catcaatgct    1740
aatccgatgg gcaaaaacat cagcattatt tttaaggctg gagatgatct tcgtcaggat    1800
atgcttgttc tgcagcttat tcaagtgatg gacaatattt ggctgcagga aggcttggat    1860
atgcaaatga tcatttatag atgtctatcc acaggaaaag accaaggatt ggtgcagatg    1920
gtacctgatg ctgtgaccct agcaaagatt catcgccatt ctggactgat aggaccattg    1980
aaagaaaata caattaaaaa gtggttcagt cagcacaacc acttaaaggc agattatgaa    2040
aaggccttga gaactttttt ctactcctgt gctggctggt gtgtggtaac attcatcctg    2100
ggagtatgtg accgtcacaa tgataatatc atgctgacaa agtcgggcca catgtttcat    2160
attgactttg gaaaattctt aggtcatgca caaacatttg gagggataaa aagggaccga    2220
gctccttttca tttttacttc agagatggaa tactttatta cagagggtgg gaaaaaccca    2280
cagcattttc aagattttgt ggaactttgc tgtcgtgctt ataatattat cagaaagcac    2340
agccaactgc tcttgaacct gctggaaatg atgctgtatg caggactgcc tgagctaagt    2400
ggaattcaag acctgaaata tgtgtataat aatcttcgtc cacaagacac agacctggaa    2460
gcaacaagtc attttaccaa gaaaatagag gaaagtctgg agtgtttccc tgttaaattg    2520
aataacttga tccacacact tgcacaaatg tcagccataa gccctgccaa atctacttca    2580
cagacttttc ctcaggaatc ctgtttgctg agtacaacta ggtcgattga agagcaaca    2640
attttagggt tcagcaagaa atccagtaat ctgtatctga tccaggtgac acacagcaac    2700
aacgaaacaa gcctgacaga aaaatcattt gagcagtttt caaaacttca cagccaactt    2760
cagaagcagt ttgcatcact gactctccca gagtttcctc attggtggca cctacctttt    2820
acaaattcag atcacagaag attcagagat ctaaatcatt acatggaaca gatattaaat    2880
gtatcacatg aagttacaaa cagtgattgt gtacttagct ttttcctctc tgaggctgtg    2940
caacaaacag ttgaagaatc atcacctgtg tacctaggtg agaagtttcc agacaagaag    3000
cctaaggtgc agttagtcat atcctacgag gatgtgaagc tgaccatact agtgaaacac    3060
atgaaaaaca ttcatctccc agatggctct gcgcccagtg cacatgttga attttatctt    3120
```

```
ttaccatatc ccagtgaagt tcgtaggagg aaaacaaaat ctgttccaaa atgtacggac    3180
cccacttaca atgaaattgt agtatatgat gaagtcacag agctccaagg acatgtctta    3240
atgcttattg tgaagagtaa aactgtattt gtgggagcaa ttaacatccg actctgtagt    3300
gtcccactcg ataaagaaaa atggtatcca ttaggaaaca gtataatttg a             3351
```

<210> SEQ ID NO 2
<211> LENGTH: 1116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Met Ala Ala Pro Leu Leu Leu Leu Leu Val Pro Val Pro
1               5                   10                  15

Leu Leu Pro Leu Leu Ala Gln Gly Pro Gly Gly Ala Leu Gly Asn Arg
                20                  25                  30

His Ala Val Tyr Trp Asn Ser Ser Asn Gln His Leu Arg Arg Glu Gly
            35                  40                  45

Tyr Thr Val Gln Val Asn Val Asn Asp Tyr Leu Asp Ile Tyr Cys Pro
        50                  55                  60

His Tyr Asn Ser Ser Gly Val Gly Pro Gly Ala Gly Pro Gly Pro Gly
65                  70                  75                  80

Gly Gly Ala Glu Gln Tyr Val Leu Tyr Met Val Ser Arg Asn Gly Tyr
                85                  90                  95

Arg Thr Cys Asn Ala Ser Gln Gly Phe Lys Arg Trp Glu Cys Asn Arg
            100                 105                 110

Pro His Ala Pro His Ser Pro Ile Lys Phe Ser Glu Lys Phe Gln Arg
        115                 120                 125

Tyr Ser Ala Phe Ser Leu Gly Tyr Glu Phe His Ala Gly His Glu Tyr
    130                 135                 140

Tyr Tyr Ile Cys Leu Ile Glu Lys Val Thr Thr Glu Leu Ser Thr Ser
145                 150                 155                 160

Ile Tyr Gln Leu Ile Asn Val Tyr Cys Asn Ser Phe Tyr Ala Asp Phe
                165                 170                 175

Gln Pro Val Asn Val Pro Arg Cys Thr Ser Tyr Leu Asn Pro Gly Leu
            180                 185                 190

Pro Ser His Leu Ser Phe Thr Val Tyr Ala Ala His Asn Ile Pro Glu
        195                 200                 205

Thr Trp Val His Arg Ile Asn Phe Pro Leu Glu Ile Lys Ser Leu Pro
    210                 215                 220

Arg Glu Ser Met Leu Thr Val Lys Leu Phe Gly Ile Ala Cys Ala Thr
225                 230                 235                 240

Asn Asn Ala Asn Leu Leu Ala Trp Thr Cys Leu Pro Leu Phe Pro Lys
                245                 250                 255

Glu Lys Ser Ile Leu Gly Ser Met Leu Phe Ser Met Thr Leu Gln Ser
            260                 265                 270

Glu Pro Pro Val Glu Met Ile Thr Pro Gly Val Trp Asp Val Ser Gln
        275                 280                 285

Pro Ser Pro Val Thr Leu Gln Ile Asp Phe Pro Ala Thr Gly Trp Glu
    290                 295                 300

Tyr Met Lys Pro Asp Ser Glu Glu Asn Arg Ser Asn Leu Glu Glu Pro
```

-continued

```
              305                 310                 315                 320
        Leu Lys Glu Cys Ile Lys His Ile Ala Arg Leu Ser Gln Lys Gln Thr
                        325                 330                 335

Pro Leu Leu Leu Ser Glu Glu Lys Lys Arg Tyr Leu Trp Phe Tyr Arg
                        340                 345                 350

Phe Tyr Cys Asn Asn Glu Asn Cys Ser Leu Pro Leu Val Leu Gly Ser
                        355                 360                 365

Ala Pro Gly Trp Asp Glu Arg Thr Val Ser Glu Met His Thr Ile Leu
                        370                 375                 380

Arg Arg Trp Thr Phe Ser Gln Pro Leu Glu Ala Leu Gly Leu Leu Thr
        385                 390                 395                 400

Ser Ser Phe Pro Asp Gln Glu Ile Arg Lys Val Ala Val Gln Gln Leu
                        405                 410                 415

Asp Asn Leu Leu Asn Asp Glu Leu Leu Glu Tyr Leu Pro Gln Leu Val
                        420                 425                 430

Gln Ala Val Lys Phe Glu Trp Asn Leu Glu Ser Pro Leu Val Gln Leu
                        435                 440                 445

Leu Leu His Arg Ser Leu Gln Ser Ile Gln Val Ala His Arg Leu Tyr
                        450                 455                 460

Trp Leu Leu Lys Asn Ala Glu Asn Glu Ala Tyr Phe Lys Ser Trp Tyr
        465                 470                 475                 480

Gln Lys Leu Leu Ala Ala Leu Gln Phe Cys Ala Gly Lys Ala Leu Asn
                        485                 490                 495

Asp Glu Phe Ser Lys Glu Gln Lys Leu Ile Lys Ile Leu Gly Asp Ile
                        500                 505                 510

Gly Glu Arg Val Lys Ser Ala Ser Asp His Gln Arg Gln Glu Val Leu
                        515                 520                 525

Lys Lys Glu Ile Gly Arg Leu Glu Glu Phe Phe Gln Asp Val Asn Thr
                        530                 535                 540

Cys His Leu Pro Leu Asn Pro Ala Leu Cys Ile Lys Gly Ile Asp His
        545                 550                 555                 560

Asp Ala Cys Ser Tyr Phe Thr Ser Asn Ala Leu Pro Leu Lys Ile Thr
                        565                 570                 575

Phe Ile Asn Ala Asn Pro Met Gly Lys Asn Ile Ser Ile Ile Phe Lys
                        580                 585                 590

Ala Gly Asp Asp Leu Arg Gln Asp Met Leu Val Leu Gln Leu Ile Gln
                        595                 600                 605

Val Met Asp Asn Ile Trp Leu Gln Glu Gly Leu Asp Met Gln Met Ile
                        610                 615                 620

Ile Tyr Arg Cys Leu Ser Thr Gly Lys Asp Gln Gly Leu Val Gln Met
        625                 630                 635                 640

Val Pro Asp Ala Val Thr Leu Ala Lys Ile His Arg His Ser Gly Leu
                        645                 650                 655

Ile Gly Pro Leu Lys Glu Asn Thr Ile Lys Lys Trp Phe Ser Gln His
                        660                 665                 670

Asn His Leu Lys Ala Asp Tyr Glu Lys Ala Leu Arg Asn Phe Phe Tyr
                        675                 680                 685

Ser Cys Ala Gly Trp Cys Val Val Thr Phe Ile Leu Gly Val Cys Asp
                        690                 695                 700

Arg His Asn Asp Asn Ile Met Leu Thr Lys Ser Gly His Met Phe His
        705                 710                 715                 720

Ile Asp Phe Gly Lys Phe Leu Gly His Ala Gln Thr Phe Gly Gly Ile
                        725                 730                 735
```

```
Lys Arg Asp Arg Ala Pro Phe Ile Phe Thr Ser Glu Met Glu Tyr Phe
            740                 745                 750
Ile Thr Glu Gly Gly Lys Asn Pro Gln His Phe Gln Asp Phe Val Glu
            755                 760                 765
Leu Cys Cys Arg Ala Tyr Asn Ile Ile Arg Lys His Ser Gln Leu Leu
    770                 775                 780
Leu Asn Leu Leu Glu Met Met Leu Tyr Ala Gly Leu Pro Glu Leu Ser
785                 790                 795                 800
Gly Ile Gln Asp Leu Lys Tyr Val Tyr Asn Asn Leu Arg Pro Gln Asp
                805                 810                 815
Thr Asp Leu Glu Ala Thr Ser His Phe Thr Lys Lys Ile Lys Glu Ser
            820                 825                 830
Leu Glu Cys Phe Pro Val Lys Leu Asn Asn Leu Ile His Thr Leu Ala
        835                 840                 845
Gln Met Ser Ala Ile Ser Pro Ala Lys Ser Thr Ser Gln Thr Phe Pro
    850                 855                 860
Gln Glu Ser Cys Leu Leu Ser Thr Thr Arg Ser Ile Glu Arg Ala Thr
865                 870                 875                 880
Ile Leu Gly Phe Ser Lys Lys Ser Ser Asn Leu Tyr Leu Ile Gln Val
                885                 890                 895
Thr His Ser Asn Asn Glu Thr Ser Leu Thr Glu Lys Ser Phe Glu Gln
            900                 905                 910
Phe Ser Lys Leu His Ser Gln Leu Gln Lys Gln Phe Ala Ser Leu Thr
        915                 920                 925
Leu Pro Glu Phe Pro His Trp Trp His Leu Pro Phe Thr Asn Ser Asp
    930                 935                 940
His Arg Arg Phe Arg Asp Leu Asn His Tyr Met Glu Gln Ile Leu Asn
945                 950                 955                 960
Val Ser His Glu Val Thr Asn Ser Asp Cys Val Leu Ser Phe Phe Leu
                965                 970                 975
Ser Glu Ala Val Gln Gln Thr Val Glu Glu Ser Ser Pro Val Tyr Leu
            980                 985                 990
Gly Glu Lys Phe Pro Asp Lys Lys  Pro Lys Val Gln Leu  Val Ile Ser
        995                 1000                 1005
Tyr Glu  Asp Val Lys Leu Thr  Ile Leu Val Lys His  Met Lys Asn
    1010                 1015                 1020
Ile His  Leu Pro Asp Gly Ser  Ala Pro Ser Ala His  Val Glu Phe
    1025                 1030                 1035
Tyr Leu  Leu Pro Tyr Pro Ser  Glu Val Arg Arg Arg  Lys Thr Lys
    1040                 1045                 1050
Ser Val  Pro Lys Cys Thr Asp  Pro Thr Tyr Asn Glu  Ile Val Val
    1055                 1060                 1065
Tyr Asp  Glu Val Thr Glu Leu  Gln Gly His Val Leu  Met Leu Ile
    1070                 1075                 1080
Val Lys  Ser Lys Thr Val Phe  Val Gly Ala Ile Asn  Ile Arg Leu
    1085                 1090                 1095
Cys Ser  Val Pro Leu Asp Lys  Glu Lys Trp Tyr Pro  Leu Gly Asn
    1100                 1105                 1110
Ser Ile  Ile
    1115

<210> SEQ ID NO 3
<211> LENGTH: 4308
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
atgtatggaa gtgcccgctc tgttgggaag gtggagccga gcagccagag ccctgggcgt      60
tcacccaggc ttccacgttc ccctcgcttg ggtcaccgtc gaaccaacag tacgggaggg     120
agttcgggaa gcagtgttgg aggtggcagt gggaaaaccc tttcaatgga aaatatacaa     180
tctttaaatg ctgcctatgc cacctctggc cctatgtatc taagtgacca tgaaaatgtg     240
ggttcagaaa cacctaaaag caccatgaca cttggccgtt ctgggggacg tctgccttac     300
ggtgttcgga tgactgctat gggtagtagc cccaatatag ctagcagtgg ggttgctagt     360
gacaccatag catttggaga gcatcacctc cctcctgtga gtatggcatc cactgtacct     420
cactcccttc gtcaggcgag agataacaca atcatggatc tgcagacaca gctgaaggaa     480
gtattaagag aaaatgatct cttgcggaag gatgtggaag taaggagag caaattgagt     540
tcttcaatga atagcatcaa gaccttctgg agcccagagc tgaagaagga acgagccctg     600
agaaaagatg aagcttccaa aatcaccatt tggaaggaac agtacagagt tgtacaggag     660
gaaaaccagc acatgcagat gacaatccag gctctccagg atgaattgcg gatccagagg     720
gacctgaatc agctgtttca gcaggatagt agcagcagga ctggcgaacc ttgtgtagca     780
gagctgacag aggagaactt tcagaggctt catgctgagc atgagcggca ggccaaagag     840
ctgtttcttc ttcgaaagac attggaggaa atggagctgc gtattgagac tcaaaagcag     900
accctaaatg ctcgggatga atccattaag aagcttctgg aaatgttgca gagcaaagga     960
ctttctgcca aggctaccga ggaagaccat gagagaacaa gacgactggc agaggcagag    1020
atgcacgttc atcacctaga aagccttttg gagcagaagg aaaaagagaa cagtatgttg    1080
agagaggaga tgcatcgaag gtttgagaat gctcctgatt ctgccaaaac aaaagctctg    1140
caaactgtta ttgagatgaa ggattcaaaa atttcctcta tggagcgtgg gcttcgagac    1200
ctggaagagg aaattcagat gctgaaatcg aatggtgctt tgagtactga ggaaagggaa    1260
gaagaaatga gcaaatggaa agtgtatcgg agccattcta aatttatgaa aaataaggta    1320
gaacaactga aggaggaact aagttcgaaa gaggctcaat gggaggagct gaaaaagaaa    1380
gcggctggtc ttcaggctga gattggccag gtgaaacagg agctgtccag aaaggacaca    1440
gaactactcg ccctgcagac aaagctagaa acactcacaa accagttctc agatagtaaa    1500
cagcacattg aagtgttgaa ggagtccttg actgctaagg agcagagggc tgccatcctg    1560
cagactgagg tggatgctct ccgattgcgt ttggaagaga aggaaaccat gttgaataaa    1620
aagacaaaac aaattcagga tatggctgaa gagaagggga cacaagctgg agagatacat    1680
gacctcaagg acatgttgga tgtgaaggag cggaaggtta atgttcttca agaagaagatt   1740
gaaaatcttc aagagcagct tagagacaag gaaaagcaga tgagcagctt gaaagaacgg    1800
gtcaaatcct tgcaggctga caccaccaac actgacactg ccttgacaac tttggaggag    1860
gcccttgcag agaaagagcg gacaattgaa cgcttaaagg agcagaggga cagagatgag    1920
cgagagaagc aagaggaaat tgataactac aaaaaagatc ttaaagactt gaaggaaaaa    1980
gtcagcctgt gcaaggcga cctttcgag aaagaggctt cacttttgga tctgaaagag      2040
catgcttctt ctctggcatc ctcaggactg aaaaaggact cacggcttaa gacactagag    2100
```

-continued

```
attgctttgg agcagaagaa ggaggagtgt ctgaaaatgg aatcacaatt gaaaaaggca    2160
catgaggcag cattggaagc cagagccagt ccagagatga gtgaccgaat acagcacttg    2220
gagagagaga tcaccaggta caaagatgaa tctagcaagg cccaggcaga agttgatcga    2280
ctcttagaaa tcttgaagga ggtggaaaat gagaagaatg acaaagataa gaagatagct    2340
gagttggaaa ggctgctaaa aaatgcagaa aatgaagctt attttaaaag ctggtatcag    2400
aagctactag ctgctctcca attctgtgca ggtaaagcct tgaatgatga gttttccaag    2460
gagcagaaac ttatcaaaat tctgggagat attggggaaa gagtcaagtc tgccagtgac    2520
catcaaagac aggaggtact gaagaaagaa attggcagac tagaagagtt ctttcaagat    2580
gtaaatactt gtcatcttcc tctgaaccct gccctatgta taaaagggat tgatcacgat    2640
gcatgttcat attttacatc taatgctttg ccattgaaga ttactttcat caatgctaat    2700
ccgatgggca aaaacatcag cattattttt aaggctggag atgatcttcg tcaggatatg    2760
cttgttctgc agcttattca agtgatggac aatatttggc tgcaggaagg cttggatatg    2820
caaatgatca tttatagatg tctatccaca ggaaaagacc aaggattggt gcagatggta    2880
cctgatgctg tgaccctagc aaagattcat cgccattctg gactgatagg accattgaaa    2940
gaaaatacaa ttaaaagtg gttcagtcag cacaaccact taaaggcaga ttatgaaaag    3000
gccttgagga acttttttcta ctcctgtgct ggctggtgtg tggtaacatt catcctggga    3060
gtatgtgacc gtcacaatga taatatcatg ctgacaaagt cgggccacat gtttcatatt    3120
gactttggaa aattcttagg tcatgcacaa acatttggag ggataaaaag ggaccgagct    3180
cctttcattt ttacttcaga gatggaatac tttattacag agggtgggaa aaacccacag    3240
cattttcaag attttgtgga actttgctgt cgtgcttata atattatcag aaagcacagc    3300
caactgctct tgaacctgct ggaaatgatg ctgtatgcag gactgcctga gctaagtgga    3360
attcaagacc tgaaatatgt gtataataat cttcgtccac aagacacaga cctggaagca    3420
acaagtcatt ttaccaagaa aataaaggaa agtctggagt gtttccctgt taaattgaat    3480
aacttgatcc acacacttgc acaaatgtca gccataagcc ctgccaaatc tacttcacag    3540
acttttcctc aggaatcctg tttgctgagt acaactaggt cgattgaaag agcaacaatt    3600
ttagggttca gcaagaaatc cagtaatctg tatctgatcc aggtgacaca cagcaacaac    3660
gaaacaagcc tgacagaaaa atcatttgag cagttttcaa aacttcacag ccaacttcag    3720
aagcagtttg catcactgac tctcccagag tttcctcatt ggtggcacct accttttaca    3780
aattcagatc acagaagatt cagagatcta aatcattaca tggaacagat attaaatgta    3840
tcacatgaag ttacaaacag tgattgtgta cttagctttt tcctctctga ggctgtgcaa    3900
caaacagttg aagaatcatc acctgtgtac ctaggtgaga gtttccaga caagaagcct    3960
aaggtgcagt tagtcatatc ctacgaggat gtgaagctga ccatactagt gaaacacatg    4020
aaaaacattc atctcccaga tggctctgcg cccagtgcac atgttgaatt ttatcttta    4080
ccatatccca gtgaagttcg taggaggaaa acaaaatctg ttccaaaatg tacggacccc    4140
acttacaatg aaattgtagt atatgatgaa gtcacagagc tccaaggaca tgtcttaatg    4200
cttattgtga agagtaaaac tgtatttgtg ggagcaatta acatccgact ctgtagtgtc    4260
ccactcgata agaaaaatg gtatccatta ggaaacagta aatttga            4308
```

<210> SEQ ID NO 4
<211> LENGTH: 1435
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 4

Met Tyr Gly Ser Ala Arg Ser Val Gly Lys Val Glu Pro Ser Ser Gln
1               5                   10                  15

Ser Pro Gly Arg Ser Pro Arg Leu Pro Arg Ser Pro Arg Leu Gly His
            20                  25                  30

Arg Arg Thr Asn Ser Thr Gly Gly Ser Ser Gly Ser Ser Val Gly Gly
        35                  40                  45

Gly Ser Gly Lys Thr Leu Ser Met Glu Asn Ile Gln Ser Leu Asn Ala
    50                  55                  60

Ala Tyr Ala Thr Ser Gly Pro Met Tyr Leu Ser Asp His Glu Asn Val
65                  70                  75                  80

Gly Ser Glu Thr Pro Lys Ser Thr Met Thr Leu Gly Arg Ser Gly Gly
                85                  90                  95

Arg Leu Pro Tyr Gly Val Arg Met Thr Ala Met Gly Ser Ser Pro Asn
            100                 105                 110

Ile Ala Ser Ser Gly Val Ala Ser Asp Thr Ile Ala Phe Gly Glu His
        115                 120                 125

His Leu Pro Pro Val Ser Met Ala Ser Thr Val Pro His Ser Leu Arg
130                 135                 140

Gln Ala Arg Asp Asn Thr Ile Met Asp Leu Gln Thr Gln Leu Lys Glu
145                 150                 155                 160

Val Leu Arg Glu Asn Asp Leu Leu Arg Lys Asp Val Glu Val Lys Glu
                165                 170                 175

Ser Lys Leu Ser Ser Ser Met Asn Ser Ile Lys Thr Phe Trp Ser Pro
            180                 185                 190

Glu Leu Lys Lys Glu Arg Ala Leu Arg Lys Asp Glu Ala Ser Lys Ile
        195                 200                 205

Thr Ile Trp Lys Glu Gln Tyr Arg Val Val Gln Glu Asn Gln His
    210                 215                 220

Met Gln Met Thr Ile Gln Ala Leu Gln Asp Glu Leu Arg Ile Gln Arg
225                 230                 235                 240

Asp Leu Asn Gln Leu Phe Gln Gln Asp Ser Ser Arg Thr Gly Glu
                245                 250                 255

Pro Cys Val Ala Glu Leu Thr Glu Glu Asn Phe Gln Arg Leu His Ala
            260                 265                 270

Glu His Glu Arg Gln Ala Lys Glu Leu Phe Leu Leu Arg Lys Thr Leu
        275                 280                 285

Glu Glu Met Glu Leu Arg Ile Glu Thr Gln Lys Gln Thr Leu Asn Ala
    290                 295                 300

Arg Asp Glu Ser Ile Lys Lys Leu Leu Glu Met Leu Gln Ser Lys Gly
305                 310                 315                 320

Leu Ser Ala Lys Ala Thr Glu Glu Asp His Glu Arg Thr Arg Arg Leu
                325                 330                 335

Ala Glu Ala Glu Met His Val His His Leu Glu Ser Leu Leu Glu Gln
            340                 345                 350

Lys Glu Lys Glu Asn Ser Met Leu Arg Glu Glu Met His Arg Arg Phe
        355                 360                 365

Glu Asn Ala Pro Asp Ser Ala Lys Thr Lys Ala Leu Gln Thr Val Ile
    370                 375                 380
```

```
Glu Met Lys Asp Ser Lys Ile Ser Ser Met Glu Arg Gly Leu Arg Asp
385                 390                 395                 400

Leu Glu Glu Glu Ile Gln Met Leu Lys Ser Asn Gly Ala Leu Ser Thr
            405                 410                 415

Glu Glu Arg Glu Glu Glu Met Lys Gln Met Glu Val Tyr Arg Ser His
        420                 425                 430

Ser Lys Phe Met Lys Asn Lys Val Glu Gln Leu Lys Glu Glu Leu Ser
    435                 440                 445

Ser Lys Glu Ala Gln Trp Glu Leu Lys Lys Ala Ala Gly Leu
450                 455                 460

Gln Ala Glu Ile Gly Gln Val Lys Gln Glu Leu Ser Arg Lys Asp Thr
465                 470                 475                 480

Glu Leu Leu Ala Leu Gln Thr Lys Leu Glu Thr Leu Thr Asn Gln Phe
            485                 490                 495

Ser Asp Ser Lys Gln His Ile Glu Val Leu Lys Glu Ser Leu Thr Ala
        500                 505                 510

Lys Glu Gln Arg Ala Ala Ile Leu Gln Thr Glu Val Asp Ala Leu Arg
    515                 520                 525

Leu Arg Leu Glu Glu Lys Glu Thr Met Leu Asn Lys Lys Thr Lys Gln
530                 535                 540

Ile Gln Asp Met Ala Glu Lys Gly Thr Gln Ala Gly Glu Ile His
545                 550                 555                 560

Asp Leu Lys Asp Met Leu Asp Val Lys Glu Arg Lys Val Asn Val Leu
            565                 570                 575

Gln Lys Lys Ile Glu Asn Leu Gln Glu Gln Leu Arg Asp Lys Glu Lys
        580                 585                 590

Gln Met Ser Ser Leu Lys Glu Arg Val Lys Ser Leu Gln Ala Asp Thr
    595                 600                 605

Thr Asn Thr Asp Thr Ala Leu Thr Thr Leu Glu Glu Ala Leu Ala Glu
610                 615                 620

Lys Glu Arg Thr Ile Glu Arg Leu Lys Glu Gln Arg Asp Arg Asp Glu
625                 630                 635                 640

Arg Glu Lys Gln Glu Glu Ile Asp Asn Tyr Lys Lys Asp Leu Lys Asp
            645                 650                 655

Leu Lys Glu Lys Val Ser Leu Leu Gln Gly Asp Leu Ser Glu Lys Glu
        660                 665                 670

Ala Ser Leu Leu Asp Leu Lys Glu His Ala Ser Ser Leu Ala Ser Ser
    675                 680                 685

Gly Leu Lys Lys Asp Ser Arg Leu Lys Thr Leu Glu Ile Ala Leu Glu
690                 695                 700

Gln Lys Lys Glu Glu Cys Leu Lys Met Glu Ser Gln Leu Lys Lys Ala
705                 710                 715                 720

His Glu Ala Ala Leu Glu Ala Arg Ala Ser Pro Glu Met Ser Asp Arg
            725                 730                 735

Ile Gln His Leu Glu Arg Glu Ile Thr Arg Tyr Lys Asp Glu Ser Ser
        740                 745                 750

Lys Ala Gln Ala Glu Val Asp Arg Leu Leu Glu Ile Leu Lys Glu Val
    755                 760                 765

Glu Asn Glu Lys Asn Asp Lys Asp Lys Lys Ile Ala Glu Leu Glu Arg
770                 775                 780

Leu Leu Lys Asn Ala Glu Asn Glu Ala Tyr Phe Lys Ser Trp Tyr Gln
785                 790                 795                 800

Lys Leu Leu Ala Ala Leu Gln Phe Cys Ala Gly Lys Ala Leu Asn Asp
```

```
                    805                 810                 815
Glu Phe Ser Lys Glu Gln Lys Leu Ile Lys Ile Leu Gly Asp Ile Gly
                820                 825                 830
Glu Arg Val Lys Ser Ala Ser Asp His Gln Arg Gln Glu Val Leu Lys
                835                 840                 845
Lys Glu Ile Gly Arg Leu Glu Glu Phe Phe Gln Asp Val Asn Thr Cys
                850                 855                 860
His Leu Pro Leu Asn Pro Ala Leu Cys Ile Lys Gly Ile Asp His Asp
865                 870                 875                 880
Ala Cys Ser Tyr Phe Thr Ser Asn Ala Leu Pro Leu Lys Ile Thr Phe
                    885                 890                 895
Ile Asn Ala Asn Pro Met Gly Lys Asn Ile Ser Ile Ile Phe Lys Ala
                900                 905                 910
Gly Asp Asp Leu Arg Gln Asp Met Leu Val Leu Gln Leu Ile Gln Val
                915                 920                 925
Met Asp Asn Ile Trp Leu Gln Glu Gly Leu Asp Met Gln Met Ile Ile
                930                 935                 940
Tyr Arg Cys Leu Ser Thr Gly Lys Asp Gln Gly Leu Val Gln Met Val
945                 950                 955                 960
Pro Asp Ala Val Thr Leu Ala Lys Ile His Arg His Ser Gly Leu Ile
                    965                 970                 975
Gly Pro Leu Lys Glu Asn Thr Ile Lys Lys Trp Phe Ser Gln His Asn
                980                 985                 990
His Leu Lys Ala Asp Tyr Glu Lys Ala Leu Arg Asn Phe Phe Tyr Ser
                    995                 1000                1005
Cys Ala Gly Trp Cys Val Val Thr Phe Ile Leu Gly Val Cys Asp
    1010                1015                1020
Arg His Asn Asp Asn Ile Met Leu Thr Lys Ser Gly His Met Phe
    1025                1030                1035
His Ile Asp Phe Gly Lys Phe Leu Gly His Ala Gln Thr Phe Gly
    1040                1045                1050
Gly Ile Lys Arg Asp Arg Ala Pro Phe Ile Phe Thr Ser Glu Met
    1055                1060                1065
Glu Tyr Phe Ile Thr Glu Gly Gly Lys Asn Pro Gln His Phe Gln
    1070                1075                1080
Asp Phe Val Glu Leu Cys Cys Arg Ala Tyr Asn Ile Ile Arg Lys
    1085                1090                1095
His Ser Gln Leu Leu Leu Asn Leu Leu Glu Met Met Leu Tyr Ala
    1100                1105                1110
Gly Leu Pro Glu Leu Ser Gly Ile Gln Asp Leu Lys Tyr Val Tyr
    1115                1120                1125
Asn Asn Leu Arg Pro Gln Asp Thr Asp Leu Glu Ala Thr Ser His
    1130                1135                1140
Phe Thr Lys Lys Ile Lys Glu Ser Leu Glu Cys Phe Pro Val Lys
    1145                1150                1155
Leu Asn Asn Leu Ile His Thr Leu Ala Gln Met Ser Ala Ile Ser
    1160                1165                1170
Pro Ala Lys Ser Thr Ser Gln Thr Phe Pro Gln Glu Ser Cys Leu
    1175                1180                1185
Leu Ser Thr Thr Arg Ser Ile Glu Arg Ala Thr Ile Leu Gly Phe
    1190                1195                1200
Ser Lys Lys Ser Ser Asn Leu Tyr Leu Ile Gln Val Thr His Ser
    1205                1210                1215
```

```
Asn Asn Glu Thr Ser Leu Thr Glu Lys Ser Phe Glu Gln Phe Ser
    1220                1225            1230

Lys Leu His Ser Gln Leu Gln Lys Gln Phe Ala Ser Leu Thr Leu
    1235                1240            1245

Pro Glu Phe Pro His Trp Trp His Leu Pro Phe Thr Asn Ser Asp
    1250                1255            1260

His Arg Arg Phe Arg Asp Leu Asn His Tyr Met Glu Gln Ile Leu
    1265                1270            1275

Asn Val Ser His Glu Val Thr Asn Ser Asp Cys Val Leu Ser Phe
    1280                1285            1290

Phe Leu Ser Glu Ala Val Gln Gln Thr Val Glu Glu Ser Ser Pro
    1295                1300            1305

Val Tyr Leu Gly Glu Lys Phe Pro Asp Lys Lys Pro Lys Val Gln
    1310                1315            1320

Leu Val Ile Ser Tyr Glu Asp Val Lys Leu Thr Ile Leu Val Lys
    1325                1330            1335

His Met Lys Asn Ile His Leu Pro Asp Gly Ser Ala Pro Ser Ala
    1340                1345            1350

His Val Glu Phe Tyr Leu Leu Pro Tyr Pro Ser Glu Val Arg Arg
    1355                1360            1365

Arg Lys Thr Lys Ser Val Pro Lys Cys Thr Asp Pro Thr Tyr Asn
    1370                1375            1380

Glu Ile Val Val Tyr Asp Glu Val Thr Glu Leu Gln Gly His Val
    1385                1390            1395

Leu Met Leu Ile Val Lys Ser Lys Thr Val Phe Val Gly Ala Ile
    1400                1405            1410

Asn Ile Arg Leu Cys Ser Val Pro Leu Asp Lys Glu Lys Trp Tyr
    1415                1420            1425

Pro Leu Gly Asn Ser Ile Ile
    1430                1435
```